United States Patent
Hu et al.

(10) Patent No.: US 8,772,043 B2
(45) Date of Patent: Jul. 8, 2014

(54) UNIVERSAL PEPTIDE TAGS FOR TRANSGENE POLYPEPTIDE ANALYSIS BY MASS SPECTROMETRY

(75) Inventors: Xuehua Hu, Johnston, IA (US);
Michaela Owens, Ankeny, IA (US);
Clara Alarcon, Altoona, IA (US);
Xiping Niu, Johnston, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 98 days.

(21) Appl. No.: 13/334,420

(22) Filed: Dec. 22, 2011

(65) Prior Publication Data

US 2012/0167238 A1  Jun. 28, 2012

Related U.S. Application Data

(60) Provisional application No. 61/426,858, filed on Dec. 23, 2010.

(51) Int. Cl.
| | | |
|---|---|---|
| *G01N 33/00* | (2006.01) | |
| *C12Q 1/68* | (2006.01) | |
| *C07K 14/00* | (2006.01) | |
| *G01N 33/68* | (2006.01) | |
| *C12N 9/10* | (2006.01) | |

(52) U.S. Cl.
CPC .............. *C12N 9/1029* (2013.01); *C07K 14/00* (2013.01); *G01N 33/6848* (2013.01); *C07K 2319/00* (2013.01); *G01N 33/6851* (2013.01)
USPC .............................................. 436/86; 435/6.1

(58) Field of Classification Search
USPC ................................. 435/6, 69.1, 6.1; 436/86
See application file for complete search history.

(56) References Cited

U.S. PATENT DOCUMENTS

| | | | |
|---|---|---|---|
| 6,824,981 B2 | 11/2004 | Chait et al. | |
| 6,872,575 B2 | 3/2005 | Regnier | |
| 7,445,907 B2 | 11/2008 | Everett et al. | |
| 2006/0078960 A1 | 4/2006 | Hunter et al. | |
| 2006/0141528 A1 | 6/2006 | Aebersold et al. | |
| 2009/0011447 A1 | 1/2009 | Banoub et al. | |

FOREIGN PATENT DOCUMENTS

WO    WO 02/084250 A2    10/2002

OTHER PUBLICATIONS

Alarcon, C., et al., "Use of epitope tags for routine analysis of transgene expression," *Transgenic Research*, 2001, vol. 10, pp. 183-192.
Anderson, L., et al., "Quantitative Mass Spectrometric Multiple Reaction Monitoring Assays for Major Plasma Proteins," *Molecular & Cellular Proteomics*, 2006, vol. 5(4), pp. 573-588.
Keshishian, H., et al., "Quantitative, Multiplexed Assays for Low Abundance Proteins in Plasma by Targeted Mass Spectrometry and Stable Isotope Dilution," *Molecular & Cellular Proteomics*, 2007, vol. 6(12), pp. 2212-2229.
"Proteomics, Peptidomics and Metabolomics," http://www.ppdi.com/services/labs/biomarker/proteomics.htm, 2009,1 page.
Wienkoop, S., et al., "Relative and absolute quantitative shotgun proteomics: targeting low-abundance proteins in *Arabidopsis thaliana*," *Journal of Experimental Botany*, 2006, vol. 57(7), pp. 1529-1535.

*Primary Examiner* — Maryam Monshipouri
(74) *Attorney, Agent, or Firm* — Pioneer Hi Bred Int'l, Inc.

(57) ABSTRACT

Compositions and methods that allow for the rapid detection and accurate quantification of any polypeptides of interest are provided. Compositions include isolated polypeptides comprising at least one universal peptide tag, as well as isolated polynucleotides encoding such polypeptides. The universal peptide tags can be quantified by methods including, but not limited to, mass spectrometry, and can act as surrogates for determining the concentration of the polypeptides comprising the universal peptide tags. Methods provide for the detection and/or quantification of any polypeptides of interest that comprise at least one universal peptide tag, including methods using mass spectroscopy techniques. Methods are also provided for producing hosts, or cells or parts thereof, that comprise polypeptides comprising at least one universal peptide tag. Hosts, or cells, or parts thereof, include mammalian, bacterial, insect, yeast, viral or plant.

10 Claims, 8 Drawing Sheets

Figure 1

Alignment of GAT Proteins

```
         SEQ ID
         NO:
GAT4601  15     (1)    -MIEVKPINAEDTYELRHRILRPNQPIEACMFESDLLRGAFHLGGFYRGK
GAT4604  16     (1)    -MIEVKPINAEDTYELRHRVLRPNQPIEACIFESDLMRGAFHLGGFYGGR
GAT4618  17     (1)    -MIEVKPINAEDTYDLRHRVLRPNQPIEACMFESDLTRSAFHLGGFYGGK
GAT4621  18     (1)    MAIEVKPINAEDTYDLRHRVLRPNQPIEACMFESDLTR*SAFHLGGFYGGK*
                       51
GAT4601  15     (50)   LISIASFHQAEHSELQGQKQYQLRGMATLEGYREQKAGSTLV
GAT4604  16     (50)   LISVASFHQAEHSELQGQKQYQLRGMATLEGYREQKAGSSLV
GAT4618  17     (50)   LISVASFHQAEHSELQGKKQYQLRGVATLEGYREQKAGSSLV
GAT4621  18     (51)   LISVASFHQAEHSELQGKKQYQLRGVATLEGYREQKAGSSLV
                       101                                              148
GAT4601  15     (100)  KRGADMLWCNARTSASGYYKKLGFSEQGEIFDTPPVGPHILMYKRIT
GAT4604  16     (100)  KRGADLLWCNARTSASGYYKKLGFSEQGEVFDTPPVGPHILMYKRIT-
GAT4618  17     (100)  KRGADMIWCNARTSASGYYRKLGFSEQGEVFDTPPVGPHILMYKRIT-
GAT4621  18     (100)  KRGADMIWCNARTSASGYYRKLGFSEQGEVFDTPPVGPHILMYKRIT-
```

Figure 2

Alignment of GAT homologues

|  | SEQ ID NO: |  | MST1 | HAEEILR |  |
|---|---|---|---|---|---|
|  |  | (98) | 98 | 110 | 122 |
| GAT 4601 | 15 | (87) | *GSS*LIK | *H*AEEILR | *KRGAD*LL*WCNAR* |
| CAA63806 | 19 | (83) | *GSA*LLK | *H*AMEKLV | *TPDLTEI*WL*NAR* |
| NP_830505 | 20 | (87) | *GSS*LIQ | *K*AEQILQ* | *ERQANM*L*WCNGR* |
| CAC98097 | 21 | (86) | *GT*ALLA | *E*GEAEIW | *KHGADII*W*CNAR* |
| ZP_00018467 | 22 | (98) | *GT*ALLD | *A*GIHYVK | *QQRGDLV*W*CHGR* |
| NP_799747 | 23 | (77) | *GSR*MLE | *M*MIEDAR | *ALNSEVF*W*CDAR* |
| Consensus | 24 | (98) | GSALL | AEE LR | ADLIWCNAR |

- N-MST-KN1
- C-MST-KN1
- N and C-KN1
- C-MST-KN1 LV
- Control: C-MST-KN1 no induction MST3-KN1-MST2 Spiked to maize leaf extract (5% v/v)

A: Null
B: DsRed2-MST3
C: Oxox-MST3

UNIVERSAL PEPTIDE TAGS FOR TRANSGENE POLYPEPTIDE ANALYSIS BY MASS SPECTROMETRY

CROSS-REFERENCE TO RELATED APPLICATIONS

This Application claims the benefit of U.S. Provisional Application 61/426,858, filed Dec. 23, 2010, herein incorporated by reference in its entirety.

FIELD OF THE INVENTION

This invention is in the field of biotechnology; in particular, this pertains to compositions and methods that allow for the rapid detection and accurate quantification of polypeptides of interest.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 410312SEQLIST.txt, created on Dec. 21, 2011, and having a size of 16 kilobytes and is filed concurrently with the specification. The sequence listing contained in this ASCII formatted document is part of the specification and is herein incorporated by reference in its entirety.

BACKGROUND

The use of transgenic host species is a powerful tool for determining the influence of specific genes on phenotypic traits and for expressing advantageous traits in desired host species. A critical step for this methodology is determining the expression and concentration of transgenic polypeptides in the host species. As transgenic technology is widely used in many industries, methods for accomplishing this step that are simple, accurate and high-throughput must be established.

Conventional screening tools, such as RT-PCR and northern blot analysis (mRNA), are limited by a statistically poor correlation between mRNA abundance and corresponding polypeptide levels. Immunoassays, such as immunoblots, radioimmunoassays and enzyme-linked immunosorbent assays (ELISAs), have several major disadvantages. They rely heavily on high quality antibodies that are not always obtainable for weakly or non-immunoreactive antigens. Additionally, membrane and membrane-associated polypeptides present great challenges to immunoassays, especially ELISAs. Furthermore, development of an immunoassay is both costly and time-consuming, usually requiring several months to years for development and validation. The utilization of epitope tags in immunoassays also has the potential disadvantage of having the secondary structure of the polypeptide mask the epitope tag, preventing accurate quantification.

Liquid chromatography coupled with tandem mass spectrometry (LC-MS/MS) has been an indispensible analytical tool to quantify small molecules including pharmaceuticals (Xu et al. (2007) *J Pharm Biomed Anal* 44:342-355) and pesticide residues (Wong et al. (2010) *J Agric Food Chem* 58:5897-5903). LC-MS/MS has also been applied to polypeptide quantification in polypeptide biomarker research (Carr and Anderson (2008) *Clin Chem* 54:1749-1752; Keshishian et al. (2007) *Mol Cell Proteomics* 6:2212-2229; Seegmiller et al. (2009) *Clin Chem* 55:1100-1107). Some literature focuses on relative quantification using isotope labeling techniques (Gygi et al. (1999) *Nat Biotechnol* 17:994-999; Ong et al. (2002) *Mol Cell Proteomics* 1:376-386; Ross et al. (2004) *Mol Cell Proteomics* 3:1154-1169), and in other cases absolute polypeptide quantification has been accomplished either by isotope dilution or using a calibration curve generated with peptide standards (Gerber et al. (2003) *Proc Natl Acad Sci USA* 100:6940-6945; Wienkoop et al. (2006) *J Exp Bot* 57:1529-1535; Kuhn et al. (2004) *Proteomics* 4:1175-1186; Lin et al. (2006) *Anal Chem* 78:5762-5767). In all cases polypeptide quantification using LC-MS/MS has been accomplished by detecting signature peptides, specific amino acid sequences naturally occurring within the polypeptide that are readily detectable by LC-MS/MS and can be used as surrogates to determine polypeptide concentration. However, this technique is limited, as new signature peptides must be identified and validated for each new polypeptide of interest. In most cases a protein of interest is needed for the method development and validation. Therefore method development cannot be done in high-throughput way for large numbers of new proteins.

In consideration of the large number of transgenes being tested in various industries and applications, it remains critically important to develop new high-throughput polypeptide detection and quantification methods that are sensitive, specific and applicable to a wide range of transgenic polypeptides of interest. Furthermore, such methods should have the advantages of shorter development time and reduced cost.

SUMMARY OF THE INVENTION

Compositions and methods that allow for the rapid detection and accurate quantification of polypeptides of interest are provided. In one embodiment, the compositions include isolated polypeptides comprising at least one universal peptide tag, as well as isolated polynucleotides encoding such polypeptides. The universal peptide tags can be quantified by methods including, but not limited to, mass spectrometry, and can subsequently act as surrogates for determining the concentration of the polypeptides with which they are fused or associated. As such, the addition of one or more universal peptide tags to a polypeptide of interest allows for rapid detection and accurate quantification of such polypeptides in a transgenic host, or cell or part thereof. Furthermore, the addition of one or more universal peptide tags to a polypeptide of interest eliminates the need to identify new signature peptides when quantifying polypeptides by mass spectrometry.

Methods provide for the detection and quantification of polypeptides of interest that have at least one universal peptide tag. In one embodiment, a sample is analyzed for the presence of universal peptide tags to determine whether the polypeptide of interest is present. In another embodiment, the universal peptide tags are quantified and used as surrogates for determining the concentration of the polypeptide of interest in the sample. In another embodiment, detection and quantification of the universal peptide tags can be accomplished using mass spectrometry. Methods are also provided for producing hosts, or cells, or parts thereof, that comprise polypeptides of interest having at least one universal peptide tag. In various embodiments, such hosts, or cells, or parts thereof, are mammalian, bacterial, insect, yeast or plant.

The following are encompassed:

1. An isolated polypeptide comprising at least one universal peptide tag, wherein said at least one universal peptide tag, or variant or fragment thereof, is incorporated into the amino acid sequence of said polypeptide.

2. The polypeptide of 1, wherein said polypeptide comprises at least two universal peptide tags.

3. The polypeptide of 2, wherein each of said universal peptide tags is identical.

4. The polypeptide of 2, wherein one of said universal peptide tags is unique.

5. The polypeptide of any of the preceding, wherein said at least one universal peptide tag comprises an amino acid sequence set forth in SEQ ID NO: 1, 3, 5, 7, 9, 11, 16, 17, 18 or 19, or an amino acid sequence having at least 80% sequence identity to SEQ ID NO: 1, 3, 5, 7, 9, 11, 16, 17, 18 or 19, wherein said at least one universal peptide tag can be detected by mass spectrometry and used to determine the presence or concentration of said polypeptide in a sample.

6. The polypeptide of any one of 1-5, wherein said at least one universal peptide tag is fused to the N-terminus of the polypeptide.

7. The polypeptide of any one of 1-5, wherein said at least one universal peptide tag is fused to the C-terminus of the polypeptide.

8. The polypeptide of any one 1-5, wherein said at least one universal peptide tag is incorporated into the amino acid sequence of the polypeptide and is not located at the N-terminus or C-terminus.

9. The polypeptide of any one of the preceding, wherein a linker peptide is positioned between said at least one universal peptide tag and the amino acid sequence of said polypeptide.

10. The polypeptide of 9, wherein said linker peptide comprises an amino acid sequence set forth in SEQ ID NO: 13.

11. A host, or cell or part thereof, comprising the polypeptide of any one of the preceding.

12. A polynucleotide comprising a nucleotide sequence, wherein said nucleotide sequence encodes the polypeptide of any one of preceding.

13. The polynucleotide of 12, wherein said nucleotide sequence comprises a sequence selected from the group consisting of:
   a. a sequence encoding the polypeptide of SEQ ID NO: 1, 3, 5, 7, 9, 11, 16, 17, 18 or 19;
   b. a sequence encoding a polypeptide having at least 80% sequence identity to SEQ ID NO: 1, 3, 5, 7, 9, 11, 16, 17, 18 or 19; and,
   c. the sequence of SEQ ID NO: 2, 4, 6, 8, 10, 12 or 15.

14. An expression cassette comprising the nucleotide sequence of 12 or 13.

15. A host, or cell, or part thereof, comprising the expression cassette of 14.

16. The host, or cell or part thereof, of 11 or 15, wherein said host is a mammal, an insect, a bacteria, a virus, or a yeast.

17. The host, or cell or part thereof, of 11 or 15, wherein said host is a plant.

18. The host, or cell or part thereof, of 17, wherein said plant is a monocot or a dicot.

19. The host, or cell or part thereof, of 18, wherein said plant is maize, wheat, barley, sorghum, rye, soybean, alfalfa, oilseed, *Brassica*, cotton, sunflower, sugarcane, potato, *Arabidopsis*, tobacco, or tomato.

20. A method of producing a host, or cell or part thereof, wherein said host comprises a polypeptide, wherein said polypeptide comprises at least one universal peptide tag, wherein said at least one universal peptide tag is incorporated into the amino acid sequence of said polypeptide, said method comprising:
   a. introducing a polynucleotide into said host, or cell or part thereof, wherein the polynucleotide encodes said polypeptide; and,
   b. expressing said polypeptide in said host, or cell or part thereof.

21. A method of detecting a polypeptide in a host, or cell or part thereof, wherein said polypeptide comprises at least one universal peptide tag, wherein said at least one universal peptide tag is incorporated into the amino acid sequence of said polypeptide, said method comprising:
   a. analyzing a sample for the presence of said at least one universal peptide tag in said host, or cell or part thereof; and,
   b. detecting the presence of said polypeptide based on the presence of said at least one universal peptide tag in said sample.

22. The method of 21, further comprising calculating the concentration of said polypeptide in said host, or cell, or part thereof, said calculating comprising:
   a. determining the concentration of said at least one universal peptide tag in said host, or cell, or part thereof; and,
   b. calculating the concentration of said polypeptide based on the concentration of said at least one universal peptide tag.

23. The method of 21 or 22, wherein said at least one universal peptide tag is detected in said host, or cell, or part thereof, by mass spectrometry, wherein the detection of said at least one signature peptide by mass spectrometry comprises:
   a. obtaining a sample of said host, or cell, or part thereof;
   b. extracting the polypeptide content of said sample to produce a polypeptide extract;
   c. digesting the polypeptide content in the extract using trypsin and/or other proteases; and,
   d. analyzing said at least one universal peptide tag using LC-MS/MS.

24. The method of 23, further comprising:
   e. analyzing an appropriate control using mass spectrometry;
   f. determining if said appropriate control produces a peak at the same retention time as said peak corresponding to said at least one universal peptide tag; and,
   g. comparing said peak from said appropriate control to said peak corresponding to said at least one universal peptide tag to determine whether said polypeptide is present in said sample.

25. The method of 23, further comprising:
   e. using stable isotope labeling or a correlation curve to determine a concentration of said at least one universal peptide tag in said sample; and,
   f. determining a concentration of said polypeptide based on said concentration determined for said at least one universal peptide tag.

26. The method of any one of 23-25, wherein the mass spectrometry is performed using a tandem mass spectrometer.

27. The method of 26, wherein said tandem mass spectrometer is used to perform liquid chromatography tandem mass spectrometry.

28. The method of 27, wherein multiple reaction monitoring is used.

29. The method of any one of 20-28, wherein said polypeptide comprises at least two universal peptide tags.

30. The method of 29, wherein each of said universal peptide tags is identical.

31. The method of 29, wherein at least one of said universal peptide tags is unique.

32. The method of any one of 20-31, wherein said at least one universal peptide tag comprises an amino acid sequence set forth in SEQ ID NO: 1, 3, 5, 7, 9, 11, 16, 17, 18 or 19, or an amino acid sequence having at least 80% sequence identity to SEQ ID NO: 1, 3, 5, 7, 9, 11, 16, 17, 18 or 19, wherein said at least one universal peptide tag can be detected by mass spectrometry and used to determine the presence or concentration of said polypeptide in a sample.

33. The method of any one of 20-32, wherein said at least one universal peptide tag is fused to the N-terminus of the polypeptide.

34. The method of any one of 20-32, wherein said at least one universal peptide tag is fused to the C-terminus of the polypeptide.

35. The method of any one 20-32, wherein said at least one universal peptide tag is incorporated into the amino acid sequence of the polypeptide and is not located at the N-terminus or C-terminus.

36. The method of any one of 20-35, wherein a linker peptide is positioned between said at least one universal peptide tag and the amino acid sequence of said polypeptide.

37. The method of 36, wherein said linker peptide comprises an amino acid sequence set forth in SEQ ID NO: 13.

38. The method of any one of 32-37, wherein said polynucleotide comprises a nucleotide sequence, wherein said nucleotide sequence is selected from the group consisting of:
 a. a nucleotide sequence encoding the polypeptide of SEQ ID NO: 1, 3, 5, 7, 9, 11, 16, 17, 18 or 19
 b. the nucleotide sequence encoding a polypeptide having at least 80% sequence identity to SEQ ID NO: 1, 3, 5, 7, 9, 11, 16, 17, 18 or 19; and,
 c. the nucleotide sequence of SEQ ID NO: 2, 4, 6, 8, 10, 12 or 15.

39. The method of any one of 20-38, wherein said host is a mammal, an insect, a bacteria, a virus, or a yeast.

40. The method of any one of 20-38, wherein said host is a plant.

41. The method of 40, wherein said plant is a monocot or a dicot.

42. The method of 41, wherein said plant is maize, wheat, barley, sorghum, rye, soybean, alfalfa, oilseed, *Brassica*, cotton, sunflower, potato, sugarcane, *Arabidopsis*, tobacco or tomato.

BRIEF DESCRIPTION OF THE DRAWINGS

FIG. 1 sets forth a sequence alignment of four GAT proteins containing signature peptide sequences.

FIG. 2 sets forth a sequence alignment of GAT homologues.

DETAILED DESCRIPTION

Figure 3:
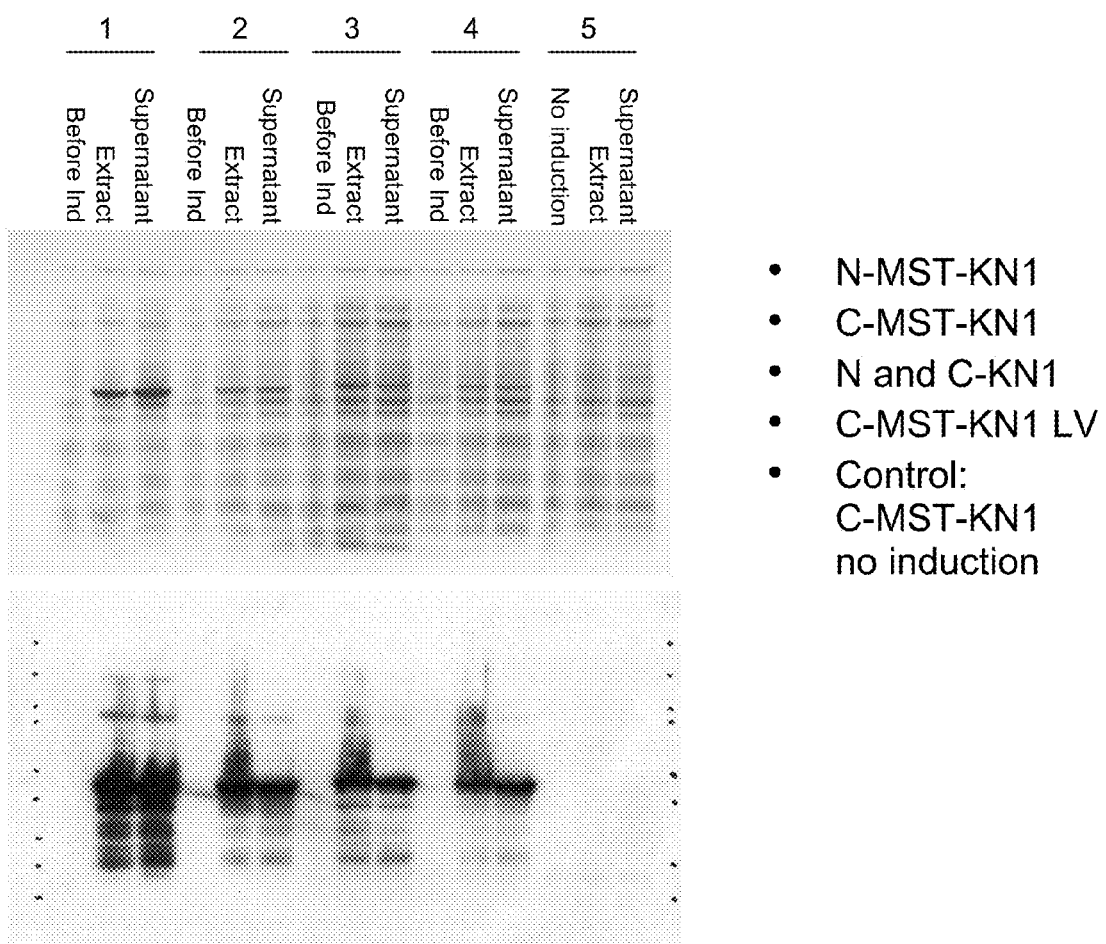
FIG. 3 shows induction of MST-KN1 polypeptides and analysis of protein extracts by total protein staining and immunoblot.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Many modifications and other embodiments of the invention set forth herein will come to mind to one skilled in the art to which the invention pertain having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Compositions and methods that allow for the rapid detection and accurate quantification of polypeptides of interest, more particularly heterologous polypeptides that are expressed in a host, or cell, or part thereof are provided. Compositions include isolated polypeptides comprising at least one universal peptide tag, as well as isolated polynucleotides encoding such polypeptides. The universal peptide tags can be quantified by methods including, but not limited to, mass spectrometry, and can subsequently act as surrogates for determining the concentration of the polypeptides with which they are fused or associated. As such, the addition of one or more universal peptide tags to a polypeptide of interest allows for rapid detection and accurate quantification of such polypeptides in a transgenic host, or cell or part thereof. Furthermore, the addition of one or more universal peptide tags to a polypeptide of interest eliminates the need to identify new signature peptides when quantifying polypeptides by mass spectrometry, and/or use of isotope labeling.

Methods provide for the detection and quantification of polypeptides of interest that have at least one universal peptide tag. In one example, a sample is analyzed for the presence of universal peptide tags to determine whether the polypeptide of interest is present. In other examples, the universal peptide tags are quantified and used as surrogates for determining the concentration of the polypeptide of interest in the sample. Other examples include detection and quantification of the universal peptide tags by accomplished using mass spectrometry. Methods are also provided for producing hosts, or cells, or parts thereof, that comprise polypeptides of interest having at least one universal peptide tag. In various examples, such hosts, or cells, or parts thereof, are mammalian, bacterial, insect, viral, yeast or plant.

It is recognized that the universal peptide tag can be used to detect or quantify any protein or polypeptide of interest. In particular, the methods find use in the detection and quantification of transgenes in an organism.

I. Universal Peptide Tags, Tagged Polypeptides, and Polynucleotides

Compositions include isolated polypeptides of interest comprising at least one universal peptide tag, referred to herein as "tagged polypeptides." Compositions also include polynucleotides encoding such tagged polypeptides, and expression cassettes comprising these polynucleotides. The polynucleotides and/or expression cassettes comprising the polynucleotides can be introduced into a host of interest. When the host, or cells, or part thereof, is cultured under conditions suitable for expression, the presence of the universal peptide tag(s) on the expressed polypeptide of interest allows for its rapid detection and accurate quantification.

As used herein "universal peptide tag" is defined as a heterologous peptide sequence that is incorporated into or fused to a polypeptide of interest, and which serves as a detectable label that facilitates identification and/or quantification of the polypeptide of interest. By "detectable label" is intended that the universal peptide tag is able to be detected in a sample of interest. In some examples, the universal peptide tag advantageously produces a signal that is detectable by mass spectrometry. Although it is recognized that the peptide sequence of the universal peptide tag can be an artificial sequence (i.e., a string of amino acid residues that do not occur in nature), in some examples the peptide sequence is derived from a naturally occurring polypeptide, or from a variant of a naturally occurring polypeptide (e.g., a mutagenized variant or one resulting from gene shuffling). Thus, in some examples, the polypeptides of interest comprise at least one universal peptide tag derived from a naturally occurring polypeptide or variant thereof, where the universal peptide tag(s) is (are) incorporated into or are fused to the polypeptide of interest, and serve(s) as a label that is detectable by mass spectrometry. It is recognized that any peptide can be used as a universal peptide tag as long as the peptide is capable of detection by mass spectrometry. Thus, the peptide tag may be naturally occurring or an artificial amino acid sequence.

As used herein, a "heterologous peptide sequence" refers to a consecutive string of amino acids which are not normally present within the naturally occurring amino acid sequence of a polypeptide of interest or, alternatively, within the genome of the organism from which the polypeptide of interest is derived. Furthermore, "a heterologous peptide sequence" may also refer to a consecutive string of amino acids which are normally present in the native amino acid sequence of a polypeptide of interest, but as a result of human intervention, are not located in their native position. In some examples, the addition of one or more universal peptide tags to a polypeptide of interest will be incorporated into the polypeptide such that they have little to no impact on the structure, function and/or activity of the native polypeptide.

In some examples, one or more universal peptide tags may be incorporated into the naturally occurring amino acid sequence of a polypeptide of interest. The universal peptide tags may be incorporated into the naturally occurring amino acid sequence of a polypeptide of interest such that there are no intervening residues located between the universal peptide tag and the naturally occurring amino acids of the polypeptide. Alternatively, one or more linker peptides may be used to attach universal peptide tags to one another or to the polypeptide of interest.

As used herein, a "linker peptide" is defined as one or more amino acid residues that are fused in frame such that they are positioned between the naturally occurring amino acids of a polypeptide of interest and a universal peptide tag, or one or more amino acid residues that are fused in frame such that they are positioned between two universal peptide tags, which in turn are incorporated into or fused to a polypeptide of interest. Linker peptides may comprise any string of amino acids that provides spacing between the polypeptide and the universal peptide tag, and/or between two universal peptide tags. Generally, the linker peptides will not produce a signal by mass spectrometry that will interfere with detection of the signal produced by the universal peptide tags. Linker peptides may have a length of at least about 1, 2, 3, 4, 5, 6, 7, 8, 9 or 10 amino acids. In the instance where the polypeptide of interest comprises more than one linker peptide, the linker peptides may comprise identical amino acid sequences, such that all of the linker peptides are the same. In the instance where the polypeptide of interest comprises more than one linker peptide, the linker peptides may also comprise different amino acid sequences, such that more than one unique linker peptide is present in the polypeptide. In one example, the linker peptide may comprise the amino acid sequence LV (SEQ ID NO:13), as shown in Table 1.

The universal peptide tags may be incorporated at the N-terminus, the C-terminus, at an internal position, both the N-terminus and C-terminus, of a polypeptide of interest, or any combination thereof. As discussed herein, linkers including linker peptides may be used to incorporate the universal peptide tags.

In examples wherein at least two universal peptide tags are incorporated into or are fused to a polypeptide of interest, each of the universal peptide tags may be identical (i.e., they comprise identical amino acid sequences). Alternatively, the universal peptide tags may comprise different amino acid sequences, such that more than one unique universal peptide tag is fused to or associated with the polypeptide.

Universal peptide tags may be of any length as long as they retain the desired function, i.e., the ability to serve as a detectable label that facilitates identification and/or quantification of the polypeptide of interest to which they are fused. In various examples, universal peptide tags may comprise at least about 5, 6, 7, 8, 9, 10, 11, 12, 13, 14, 15, 16, 17, 18, 19, 20 or more amino acids.

The universal peptide tags can be detected following cleavage of the tagged polypeptide of interest. Polypeptide cleavage may be accomplished using any suitable method known to those of skill in the art. Thus, for example, cleavage can be achieved with the use of trypsin, endopolypeptidease Glu-C, endopolypeptidease Lys-C, endopolypeptidease Asp-N, chymotrypsin, or any combination thereof. The cleavage may be accomplished at various temperatures and over varying lengths of time. Such methods for polypeptide cleavage are well known to those of ordinary skill in the art, and include, but are not limited to, the digestion methods disclosed in the Experimental section herein below. Typically, the universal peptide tag(s) will be stable during cleavage of the tagged polypeptide of interest, i.e., the universal peptide tag(s) remain(s) sufficiently intact to be detectable.

In one example, the universal peptide tags are detectable by mass spectrometry following cleavage of the tagged polypeptide. In this manner, following the cleavage process, the universal peptide tags produce a signal that is detectable by mass spectrometry. Such a signal may include, but is not limited to, a well-defined peak whose area can be quantified. As noted above, the universal peptide tag may be derived from a naturally occurring polypeptide. In such cases, the universal peptide tag is usually chosen such that the naturally occurring polypeptide from which it is derived is not endogenously produced in the host, or cell, or part thereof, in which the tagged polypeptide will be expressed. This advantageously minimizes the background of the signal obtained by mass spectrometry.

The detection of a universal peptide tag in a sample is indicative of the presence of the related polypeptide of interest to which it has been fused. Thus, the tag can be used for the detection and quantification of the polypeptide of interest. Such techniques for quantification are known in the art include, but are not limited to, stable isotope tagging of synthesized universal peptide tags with, for example, $^{13}C$ or $^{15}N$. Methods for quantifying universal peptide tags may also include the use of a correlation curve, wherein the peak produced by the universal peptide tag extracted from a sample is correlated with a standard curve created using known concentrations of synthesized universal peptide tag polypeptides in order to calculate a concentration of the universal peptide tag in the sample.

It is recognized that the amino acid residues within a universal peptide tag can be an artificial sequence (i.e., a string of amino acid residues that do not occur in nature). In some examples, the peptide sequence is derived from a naturally occurring polypeptide, or from a variant of a naturally occurring polypeptide (for example, a mutagenized variant or one resulting from gene shuffling). In such examples, the universal peptide tag may comprise the amino acid sequence of any signature peptide identified in any naturally occurring polypeptide as long as it allows for the detection and quantification of a polypeptide of interest to which it is fused. For example, signature peptides that may be used as universal peptide tags include, but are not limited to, those disclosed by Anderson and Hunter (2006) *Mol Cell Proteomics* Vol. 5:573-588, Keshishian et al. (2007) *Mol Cell Proteomics* 6:2212-2229, Zhang et al. (2008) *Rapid Commun Mass Spectrom* 22:1455-1460; and Winther et al. (2009) *J Chromatogr B Analyt Technol Biomed Life Sci* 877:1359-1365, U.S. Patent Publication No. US 2006/0141528, U.S. Patent Publication No. US 2006/0078960 and U.S. Patent Publication No. US 2009/0011447, all of which are incorporated by reference herein. Additional examples of signature peptides that may be used as universal peptide tags can be identified using publicly available databases including, but not limited to, PeptideAtlas (which can be found on the world wide web at www.peptideatlas.org) and SRMatlas (which can be found on the world wide web at www.srmatlas.org).

In one example, the signature peptides utilized as universal peptide tags will not be immunogenic, thus eliminating the need to remove the universal peptide tags from the related polypeptides of interest for regulatory concerns. As used herein, the term "immunogenic" is defined as an ability of an antigen to elicit an immune response, including a humoral or cellular-immune response. Universal peptide tags may be screened against publicly available allergenic and toxic databases to determine their potential immunogenicity.

As indicated, any peptide sequence detectable by mass spectrometry can be used as a universal peptide tag. In one example, the universal peptide tags are derived from the glyphosate N-acetyl transferase (GAT) polypeptide. Exemplary amino acid sequences for such GAT-derived universal peptide tags are described in Table 1. Each GAT-derived universal peptide tag disclosed in Table 1 was screened against allergenic and toxic databases, and it is predicted that these tags may not need to be removed from their related polypeptides of interest for regulatory concerns.

TABLE 1

GAT-derived MST universal peptide tags.

| Peptide Name | SEQ ID NO | Sequence | SEQ ID NO of nucleotide sequence |
| --- | --- | --- | --- |
| MST1 | 1 | KHAEEILR (SEQ ID NO: 1) | 2 |
| MST2 | 3 | KHGEEILR (SEQ ID NO: 3) | 4 |
| MST3 | 5 | KHVEEILR (SEQ ID NO: 5) | 6 |
| MST1-N | 7 | MIKHAEEILR (SEQ ID NO: 7) | 8 |

TABLE 1-continued

GAT-derived MST universal peptide tags.

| Peptide Name | SEQ ID NO | Sequence | SEQ ID NO of nucleotide sequence |
| --- | --- | --- | --- |
| MST2-N | 9 | MIKHGEEILR (SEQ ID NO: 9) | 10 |
| MST3-N | 11 | MIKHVEEILR (SEQ ID NO: 11) | 12 |
| Linker Peptide | 13 | LV (SEQ ID NO: 13) | 14 |

The MST1 universal peptide tag comprises the amino acid sequence KHAEEILR (SEQ ID NO: 1) and is positioned at the C-terminus of a polypeptide. MST1-N comprises the amino acid sequence MIKHAEEILR (SEQ ID NO: 4) and is positioned at the N-terminus. The MST2, MST2-N, MST3 and MST3-N universal peptide tags are variants of MST1 and MST1-N, each possessing a single amino acid mutation. The MST2 and MST2-N universal peptide tags comprise the same amino acid sequence as MST1 and MST1-N with a single amino acid substitution from A→G. Similarly, the MST3 and MST3-N universal peptide tags comprise the same amino acid sequence as MST1 and MST1-N with a single amino acid substitution from A→V. The use of MST2, MST2-N, MST3 and MST3-N, as disclosed in the Examples described herein, demonstrates the utility of variant universal peptide tags derived from a known amino acid sequence. An alignment of the amino acid sequences of multiple GAT proteins which comprise the MST1 signature peptide is presented in FIG. 1. An alignment of amino acid sequences from multiple GAT homologues is presented in FIG. 2. Using this approach, universal peptide tags can be identified for any polypeptide.

Polynucleotides encoding the tagged polypeptides are also provided. In this manner, polynucleotides comprising a coding sequence for the polypeptide of interest operably linked to a coding sequence for at least one universal peptide tag are provided herein. The coding sequence for the polypeptide of interest is fused in frame with coding sequence(s) for the universal peptide tag(s), and optionally fused in frame with coding sequence(s) for one or more linker peptides. The coding sequence for a polypeptide of interest can readily be determined from gene sequence databases known in the art. The coding sequence for a universal peptide tag to be fused to the coding sequence for the polypeptide of interest can readily be designed based upon the degeneracy of the genetic code and/or based upon the coding sequence for the naturally occurring polypeptide or variant thereof from which the universal peptide tag is derived.

II. Fragments and Variants

Once a universal peptide tag of interest has been identified it may be altered in various ways including amino acid substitutions, deletions, truncations, and insertions as long as such alterations do not change its ability to be detected by mass spectrometry. Methods for such manipulations are generally known in the art. For example, amino acid sequence variants and fragments of the universal peptide tag of interest can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Conservative substitutions, such as exchanging one amino acid with another having similar properties, may be optimal. Obviously, the mutations that will be made in the DNA encoding the variant universal peptide tag must not place the sequence out of reading frame and optimally will not create complementary regions that could produce secondary mRNA structure. See, EP Patent Application Publication No. 75,444.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect from any change will be evaluated by routine screening assays. Thus, for example, the ability of a universal peptide tag to facilitate detection of activity can be evaluated by mass spectrometry, as described herein below.

Biologically active fragments and variants of a universal peptide tag may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence of the native universal peptide tag as determined by sequence alignment programs and parameters known in the art. A fragment of a universal peptide tag may comprise at least 2, 3, 4, 5, 6, 7, 8, 9, 10, 11, 12, 13, 14, 15, 16, 17, 18, 19, 20 or more contiguous amino acids, or up to the total number of amino acids present in a full-length universal peptide tag of interest (for example, up to 8 amino acids for the MST1 signature peptide tag shown in SEQ ID NO: 1). A biologically active variant of a universal peptide tag may differ from the native universal peptide tag by as few as 1-15 amino acid residues, as few as 1-10, such as 6-10, as few as 5, as few as 4, 3, 2, or even 1 amino acid residue.

III. Expression Cassettes

The polynucleotides encoding the universal peptide tags and/or tagged polypeptides can be provided in expression cassettes for expression in a host, or cell or part thereof. The cassette may include 5' and.or 3' regulatory sequences operably linked to a polynucleotide. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two polypeptide coding regions, by operably linked is intended that the coding regions are in the same reading frame. The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain selectable marker genes.

For example, the expression cassette may include in the 5'-3' direction of transcription, a transcriptional and translational initiation region (i.e., a promoter), a polynucleotide encoding a polypeptide of interest comprising one or more universal peptide tags (and optionally coding sequences for one or more linker peptides), and a transcriptional and translational termination region (i.e., termination region) functional in the host organism. The regulatory regions (i.e., promoters, transcriptional regulatory regions, and translational termination regions) and/or the coding sequence for the polypeptide of interest may be native/analogous to the host cell or to each other. Alternatively, the regulatory regions and/or the coding sequence for the polypeptide of interest may be heterologous to the host cell or to each other. As used herein, "heterologous" is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

A heterologous promoter, or the native promoter sequence for the polypeptide of interest, may be used. Such constructs can change the levels of polypeptide expression in the host, or cell or part thereof. Thus, the phenotype of the host, or cell or part thereof, can be altered.

The termination region may be native with the transcriptional initiation region, may be native with the operably linked coding sequence for the polypeptide of interest, may be native with the host, or may be derived from another source (i.e., foreign or heterologous) to the promoter, the coding sequence for the polypeptide of interest, the host, or any combination thereof. Selection of suitable termination regions is within the means of one of ordinary skill in the art. For plant hosts, convenient termination regions may include, but are not limited to, those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be modified for increased expression in a transformed host, or cell, or part thereof. That is, the polynucleotides can be synthesized using host-preferred codons for improved expression. See, for example, Campbell and Gowri (1990) *Plant Physiol.* 92:1-11 for a discussion of host-preferred codon usage in plants. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a host, or cell or part thereof. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given host, as calculated by reference to known genes expressed in the host. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165:233-238), MDMV leader (Maize Dwarf Mosaic Virus) (Kong et al. (1988) *Arch Virol* 143:1791-1799), and human immunoglobulin heavy-chain binding polypeptide (BiP) (Macejak et al. (1991) *Nature* 353:90-94); untranslated leader from the coat polypeptide mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

IV. Detection and Quantification Using LC-MS/MS

Methods include the detection and/or quantification of polypeptides of interest comprising at least one universal peptide tag. In one example, the polypeptides are extracted from a host, or cell, or part thereof, separated by chromatography, and detected using mass spectrometry. In another example, the concentration of the universal peptide tags and, subsequently, the related polypeptides of interest, are determined in a sample by first quantifying the universal peptide tags by chromatography and mass spectrometry and then using the universal peptide tags as surrogates for determining the concentration of the tagged polypeptides of interest.

By "extracting" is intended any method that allows for the removal of the analyte of interest from the sample matrix or a sample derived therefrom. As used herein, the term "extraction" or derivations thereof does not necessarily refer to the removal of all materials or constituents other than the analyte(s) of interest from a sample matrix or a sample derived therefrom. Instead, in some examples, the term "extraction" refers to a procedure that enriches the amount of one or more analytes of interest relative to one or more other components present in the sample matrix or in a sample derived therefrom. In some examples, an "extraction" procedure can be used to remove one or more components of a sample that could interfere with the detection of the analyte, for example, one or more components that could interfere with detection of an analyte ion by mass spectrometry. In other examples, the extraction procedure is used to remove the analyte of interest from the test sample matrix, and in still other embodiments, the extraction procedure is used to purify a first analyte of interest away from a second analyte of interest in a sample or to purify an analyte of interest away from an interfering substance. Various extraction techniques known to those of ordinary skill in the art can be employed to extract and/or purify at least one of the analytes of interest (i.e., universal peptide tags) from the sample. In particular examples, the extraction techniques may utilize solvents known in the art to be useful for extraction of analytes of interest (i.e., universal peptide tags) for chromatography and mass spectrometry analysis.

Following the extraction of one or more of the analyte(s) of interest (i.e., universal peptide tags) from the test sample, any method can be employed that allows for the detection of one or more of the analytes of interest. In one example, detecting one or more of the analytes of interest comprises chromatographically separating at least one of the analytes of interest from the extracted test sample and analyzing at least one of the chromatographically separated analytes to determine the presence and/or amount of at least one universal peptide tag in the test sample.

As used herein, "chromatographically separating" employs an "analytical column" or a "chromatography column" having sufficient chromatographic plates to effect a separation of the components of a test sample matrix. In some examples, the components eluted from an analytical column are separated in such a way to allow the presence and/or amount of an analyte(s) of interest to be determined.

In some examples, analytes of interest (i.e., a universal peptide tag) are chromatographically separated from other analytes prior to detection. Depending on the method of detection employed, it may not be necessary to separate each of the analytes from one another by chromatography, thus allowing each of the analytes to be detected when present as a mixture.

In specific examples, following the extraction step, chromatographically separating the analytes of interest includes: (a) dispensing the composition comprising the extracted analyte(s) onto an analytical column; and (b) eluting the analyte(s) from the analytical column. In one example, chromatographically separating the analytes of interest from one another, or from other constituents of the test sample, comprises the use of a high performance liquid chromatography (HPLC) column. Any HPLC column that can sufficiently resolve the analytes of interest and allow for their detection and/or quantification can be employed.

In some examples, the universal peptide tag polypeptides and/or tagged polypeptides are detected and/or quantified using chromatography (e.g., HPLC) in combination with mass spectrometry. As used herein, "detecting" or "detected" is defined as determining the presence of an analyte of interest (i.e., universal peptide tags) in a test sample. The method of detection is not restricted and may be either qualitative or quantitative. In one example, detecting the universal peptide tags comprises analyzing chromatographically separated analytes using a mass spectrometer.

The term "mass spectrometry" or "MS" as used herein generally refer to methods of filtering, detecting, and measuring ions based on their mass-to-charge ratio, or "m/z." In MS techniques, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,107,623, entitled "Methods and Apparatus for Tandem Mass Spectrometry," which is hereby incorporated by reference in its entirety. Methods for using mass spectroscopy to detect and/or quantify the analytes of interest (i.e., universal peptide tags) in the samples are well-known in the art and would be within the ability of those of ordinary skill. See Hu et al. (Journal of Agricultural and Food Chemistry (submitted 2010) Multiplexed Protein Quantification in Maize Leaves by LC-MS/MS: An Alternative Tool to Immunoassays for Target Protein Analysis in Genetically Engineered Crops), which is hereby incorporated by reference.

V. Hosts

Compositions include hosts, or cells or parts thereof, that express polypeptides of interest comprising at least one universal peptide tag. As used herein, the phrase "host, or cell or part thereof" refers to any organism, or cell, or part of that organism, that can be used as a suitable host for expressing the universal peptide tags and/or tagged polypeptides. It is understood that such a phrase refers not only to the particular host, or cell or part thereof, but also to the progeny or potential progeny thereof. Because certain modifications may occur in succeeding generations due to either mutation or environmental influences, such progeny may not, in fact, be identical to the parent, but are still included within the scope of the phrase as used herein.

In one example, universal peptide tags and/or the tagged polypeptides are expressed in a prokaryotic host, or cell or part thereof, or a eukaryotic host, or cell or part thereof. In another example, the host is an invertebrate host, or cell or part thereof, or a vertebrate host, or cell or part thereof. In another example, the host, or cell or part thereof, may be, but is not limited to, a bacterium, a fungus, yeast, a nematode, an insect, a fish, a plant, an avian, an animal, or a mammal.

Mammalian hosts, or cells or parts thereof, that are suitable for expression of the polypeptides are known to those of ordinary skill in the art, and may include, but are not limited to, hamsters, mice, rats, rabbits, cats, dogs, bovine, goats, cows, pigs, horses, sheep, monkeys, or chimpanzees. Mammalian cells or mammalian parts may also be derived from humans, and the selection of such cells or parts would be known to those of ordinary skill in the art.

The selection of suitable bacterial hosts for expression of the tagged polypeptides of the invention is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.).

The selection of suitable yeast hosts for expression of the polypeptides is known to those of ordinary skill in the art, and may include, but is not limited to, ascosporogenous yeasts (Endomycetales), basidiosporogenous yeasts and yeast belonging to Fungi Imperfecti (Blastomycetes). When selecting yeast hosts for expression, suitable hosts may include those shown to have, inter alia, good secretion capacity, low proteolytic activity, and overall vigor. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md. Since the classification of yeast may change in the future, yeast shall be defined as described in Skinner et al., eds. 1980) *Biology and Activities of Yeast* (Soc. App. Bacteriol. Symp. Series No. 9).

The selection of suitable insect hosts for expression of the polypeptides is known to those of ordinary skill in the art, and may include, but is not limited to, *Aedes aegypti, Bombyx mori, Drosophila melanogaster, Spodoptera frugiperda*, and *Trichoplusia ni*. Insect cells suitable for the expression of universal peptide tags and/or tagged polypeptides include, but are not limited to, SF9 cells, and others also well known to those of ordinary skill in the art. In selecting insect hosts for expression, suitable hosts may include those shown to have, inter alia, good secretion capacity, low proteolytic activity, and overall robustness. Insect hosts are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.)

The selection of suitable plant hosts for expression of the polypeptides is known to those of ordinary skill in the art. As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Progeny, variants, and mutants of the regenerated plants are also included, provided that these parts comprise the introduced polynucleotides.

In one example, any plant species may be utilized as a host, including, but not limited to, monocots and dicots. Examples of plant species of interest include, but are not limited to, corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables of interest include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers of interest include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, magnolia, maple, oak, poplar, red alder, redbud, royal paulownia, sassafras, sweetgum, sycamore, tupelo, willow, yellow-poplar.

In specific examples, the plants or cells, or parts thereof are crop plants (for example, corn, alfalfa, sunflower, *Brassica*, soybean, cotton, safflower, peanut, sorghum, wheat, millet, tobacco, sugarcane etc.).

Other plants of interest including turfgrasses such as, for example, turfgrasses from the genus *Poa, Agrostis, Festuca, Lolium*, and *Zoysia*. Additional turfgrasses can come from the subfamily Panicoideae. Turfgrasses can further include, but are not limited to, Blue gramma (*Bouteloua gracilis* (H.B.K.) Lag. Ex Griffiths); Buffalograss (*Buchloe dactyloids* (Nutt.) Engelm.); Slender creeping red fescue (*Festuca rubra* ssp.

*Litoralis*); Red fescue (*Festuca rubra*); Colonial bentgrass (*Agrostis tenuis* Sibth.); Creeping bentgrass (*Agrostis palustris* Huds.); Fairway wheatgrass (*Agropyron cristatum* (L.) Gaertn.); Hard fescue (*Festuca longifolia* Thuill.); Kentucky bluegrass (*Poa pratensis* L.); Perennial ryegrass (*Lolium perenne* L.); Rough bluegrass (*Poa trivialis* L.); Sideoats grama (*Bouteloua curtipendula* Michx. Torr.); Smooth bromegrass (*Bromus inermis* Leyss.); Tall fescue (*Festuca arundinacea* Schreb.); Annual bluegrass (*Poa annua* L.); Annual ryegrass (*Lolium multiflorum* Lam.); Redtop (*Agrostis alba* L.); Japanese lawn grass (*Zoysia japonica*); bermudagrass (*Cynodon dactylon; Cynodon* spp. L.C. Rich; *Cynodon transvaalensis*); Seashore paspalum (*Paspalum vaginatum* Swartz); Zoysiagrass (*Zoysia* spp. Willd; *Zoysia japonica* and *Z. matrella* var. *matrella*); Bahiagrass (*Paspalum notatum* Flugge); Carpetgrass (*Axonopus affinis* Chase); Centipedegrass (*Eremochloa ophiuroides* Munro Hack.); Kikuyugrass (*Pennisetum clandesinum* Hochst Ex Chiov); Browntop bent (*Agrostis tenuis* also known as *A. capillaris*); Velvet bent (*Agrostis canina*); Perennial ryegrass (*Lolium perenne*); and, St. Augustinegrass (*Stenotaphrum secundatum* Walt. Kuntze). Additional grasses of interest include switchgrass (*Panicum virgatum*).

VI. Methods of Producing Hosts

Methods provided herein also include the production of hosts, or cells or parts thereof, that express the universal peptide tags and/or polypeptides of interest comprising at least one universal peptide tag. Methods for modulating the concentration of the polypeptides in a host, or cell or part thereof, are provided. In general, concentration is increased by at least 1%, 5%, 10%, 20%, 30%, 40%, 50%, 60%, 70%, 80%, or 90% relative to a native control host, or cell or part thereof, which did not have a sequence comprising an introduced universal peptide tag. Modulation may occur during and/or subsequent to growth of the host, or cell or part thereof, to the desired stage of development.

The expression level of the polypeptides may be measured directly, for example, by assaying for the levels of the universal peptide tags in the host, or cell or part thereof. Methods for assaying the levels of the universal peptide tags in the host, or cell or part thereof are described elsewhere herein.

In specific examples, the tagged polypeptide or a polynucleotide encoding a universal peptide tag and/or tagged polypeptide is introduced into the host, or cell or part thereof. Subsequently, the host, or cell or part thereof, having the introduced sequence may advantageously be selected using the detection methods disclosed herein, which rely on detection of a universal peptide tag, or using methods known to those of skill in the art such as, but not limited to, Southern blot analysis, DNA sequencing, PCR analysis, or phenotypic analysis. A host, or cell, or part thereof, altered or modified by one or more of the foregoing examples, is grown under appropriate conditions and for a sufficient time, both of which would be known to one of skill in the art, to modulate the concentration of the polypeptides in the host, or cell, or part thereof.

It is recognized that the methods do not depend on the incorporation of the entire polynucleotide described herein into the genome, only that the host, or cell, or part thereof, is altered as a result of the introduction of the polynucleotide. In one example, the genome may be altered following the introduction of the into a host, or cell, or part thereof. For example, the polynucleotide, or any part thereof, may incorporate into the genome of the host, or cell, or part thereof. Alterations to the genome include, but are not limited to, additions, deletions, and substitutions of nucleotides into the genome. While the methods do not depend on additions, deletions, and substitutions of any particular number of nucleotides, it is recognized that such additions, deletions, or substitutions comprise at least one nucleotide.

Methods for expressing the polypeptides in the hosts described herein are well known to those of ordinary skill in the art. Transformation of appropriate hosts with an expression cassette is accomplished by well known methods. With regard to transformation of prokaryotic hosts, see, for example, Cohen et al. (1972) Proc. Natl. Acad. Sci. USA 69:2110 and Sambrook et al. (1989) Molecular Cloning, A Laboratory Manual, Cold Spring Harbor Laboratory, Cold Spring Harbor, N.Y. Transformation of yeast is described in Sherman et al. (1986) Methods In Yeast Genetics, A Laboratory Manual, Cold Spring Harbor, N.Y. The method of Beggs (1978) Nature 275:104-109 is also useful. With regard to vertebrates, reagents useful in transfecting such hosts, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast, bacteria, insect cells and vertebrate cells.

A successfully transformed host, or cell or part thereof, i.e., one that contains a polynucleotide encoding a tagged polypeptide of interest, and which is expressing that tagged polypeptide, advantageously can be identified by the universal peptide tag detection methods described herein. A successfully transformed host, or cell or part thereof, can also be identified using well known techniques. For example, cells resulting from the introduction of an expression cassette can be grown to produce the tagged polypeptide. Cells can be harvested and lysed, and their DNA content examined for the presence of the polynucleotide encoding the tagged polypeptide using a method such as that described by Southern (1975) *J. Mol. Biol.* 98:503; or Berent et al. (1985) *Biotech.* 3:208. Alternatively, the presence of the polypeptide in the supernatant can be detected using antibodies and methods known to those of ordinary skill in the art.

In addition to directly assaying for the presence of recombinant DNA, successful transformation can be confirmed by well known immunological methods when the recombinant DNA is capable of directing the expression of the polypeptide. For example, cells successfully transformed with an expression vector produce polypeptides displaying appropriate antigenicity. Samples of cells suspected of being transformed may be harvested and assayed for the tagged polypeptide using suitable antibodies to the polypeptide of interest that has the universal peptide tag incorporated in or fused thereto.

For stable transfection of a host, or cell or part thereof, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host, or cell or part thereof, along with the gene of interest. For example, selectable markers may include those which confer resistance to drugs, such as G418, hygromycin, and methotrexate. A nucleic acid encoding a selectable marker can be introduced into a host, or cell or part thereof, on the same vector as that encoding a tagged polypeptide, or alternatively introduced on a separate vector. A host, or cell, or part thereof, that is stably transfected with the introduced nucleic acid can be identified by drug selection.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

Example 1

Over-Expression of MST-Tagged Knotted1 Polypeptides

GAT-derived signature peptides were utilized as universal peptide tags with the maize protein Knotted1, a *Ceriporiopsis subvermispora* oxalate oxidase (oxox) protein, or a DsRed2 fluorescent protein. As shown, the universal peptide tags were positioned at either the N-terminus, the C-terminus, or at both termini of their associated protein. Detection of the universal peptide tags was performed in *E. coli*, tobacco, and maize. Parameters evaluated included: the use of variant universal peptide tags, placement of universal peptide tags at one or both termini of the polypeptide, utilization of multiple universal peptide tags on the same polypeptide, and incorporation of a linker peptide between the polypeptide of interest and the universal peptide tag.

Over-Expression of MST-Tagged Knotted1 Polypeptides in *Escherichia coli*:

The full length maize Knotted1 (KN1) (Vollbrecht et al. (1991) *Nature* 350241-3) clone was identified in the Pioneer database. The CDS of KN1 was amplified by PCR with primers containing MST sequences and restriction enzyme sites for cloning. For N-terminal fusions having a universal peptide tag placed before the first amino acid of KN1, MST sequences are: MIKHAEEILR (SEQ ID NO: 7) for MST1, MIKHGEEILR (SEQ ID NO: 9) for MST2, and MIKHVEEILR (SEQ ID NO: 11) for MST3. For C-terminal fusions having a universal peptide tag placed after the last amino acid of KN1, MST sequences with a stop codon are: KHAEEILR (SEQ ID NO: 1) for MST1, KHGEEILR (SEQ ID NO: 3) for MST2, KHVEEILR (SEQ ID NO: 5) for MST3, and LVKHAEEILR (SEQ ID NO: 26) for MST1 with a linker of two amino acids (nucleotide sequence of SEQ ID NO: 25). An RcaI site was added to all the N-terminal primers in frame with the first methionine and a HindIII site was added to all the C-terminal primers after the stop codon. The PCR products were cloned into pCR4BLUNT-TOPO for sequencing (Invitrogen). The clones were digested with RcaI and HindIII, and the MST-KN1 fragments were cloned into pET28a digested with NcoI and HindIII. The resulting pET vectors were transformed into BL21 (DE3) cells. The cells were grown to about 0.4 of OD600 and induced by 0.4 mM IPTG. The polypeptides were extracted in 1×PBS buffer with 0.1% v/v Tween20. The supernatants after centrifugation were used for MS analysis.

Sample Preparation:

Fifty μL extracted samples were added to 110 μL digestion buffer (50 mM ammonium bicarbonate with 5% acetonitrile) in Eppendorf tubes. Sequencing grade modified trypsin (Promega) was added to produce a trypsin/polypeptide ratio of 1:15. Samples were mixed briefly and spun in a microcentrifuge. Samples were then placed in a CEM Discover Proteomics System. Trypsin digestion lasted for 30 min (45° C., 50 W). After acidification with 10 μL 10% (v/v) formic acid, samples were subjected to LC-MS/MS analysis.

LC-MS/MS Analysis:

The LC-MS/MS included an Applied Biosystems/MDS Sciex 4000 Q TRAP with a Turbo ion-spray source and Waters Acquity HPLC. Autosampler temperature was kept at 5° C. during analysis. Twenty microliters were injected onto an Aquasil 100×2.1 mm 3 μC18 column (ThermoFisher) kept at 60° C. LC was performed at a flow rate of 0.6 mL/min unless specified otherwise. Mobile phases consisted of 0.1% formic acid (MPA) and 0.1% formic acid in acetonitrile (MPB). The LC run started at 0% MPB for 0.2 min, followed by a 2.8-min linear gradient to 25% MPB. The column was then washed with 90% MPB (0.8 mL/min) for 1 min, followed by column equilibrium for 1 min. Total run time for each injection was approximately 6 min.

The mass spectrometer was run in multiple reaction monitoring (MRM) mode at unit-mass resolution in both Q1 and Q3 to quantify tryptic peptides: HAEEILR (SEQ ID NO: 27), HGEEILR (SEQ ID NO: 28) and HVEEILR (SEQ ID NO: 29). The following electrospray ionization source parameters were used: dwell time of 100 ms for all MRM transitions, ion-spray voltage 5500, turbo temperature 600° C., curtain gas 30, both GS1 and GS2 80, and CAD gas high. The MRM transitions of 427.2/716.1, 434.2/730.1 and 448.2/659.3 were monitored for peptides HAEEILR (SEQ ID NO: 27), HGEEILR (SEQ ID NO: 28) and HVEEILR (SEQ ID NO: 29), respectively. Various stable isotope labeled peptides such as HVEEIL*R where L is labeled with stable isotopes $^{13}$C and $^{15}$N were used as internal standards. Chromatograms were integrated using Analyst v1.4 for both analyte peptides and internal standards.

Detection of MST-KN1 Polypeptides in Cell Extracts:

MST-KN1 polypeptides were detected in cell extracts obtained from *E. coli* (FIG. 3). Induction of cells with IPTG induced the expression of N-MST-KN1, C-MST-KN1, N- and C-KN1 and C-MST-KN1 LV, which were detectable by polypeptide staining with Coomassie blue (top panel), and by immunoblot using an anti-KN1 antibody (bottom panel). Induction of MST-KN1 polypeptides is readily observable for each cell when compared to extracts from cells obtained prior to induction. Control cells, which were transfected to express C-MST-KN1, but were not induced with IPTG, did not express detectable levels of C-MST-KN1 by either Coomassie blue staining or immunoblot analysis.

Figure 4:
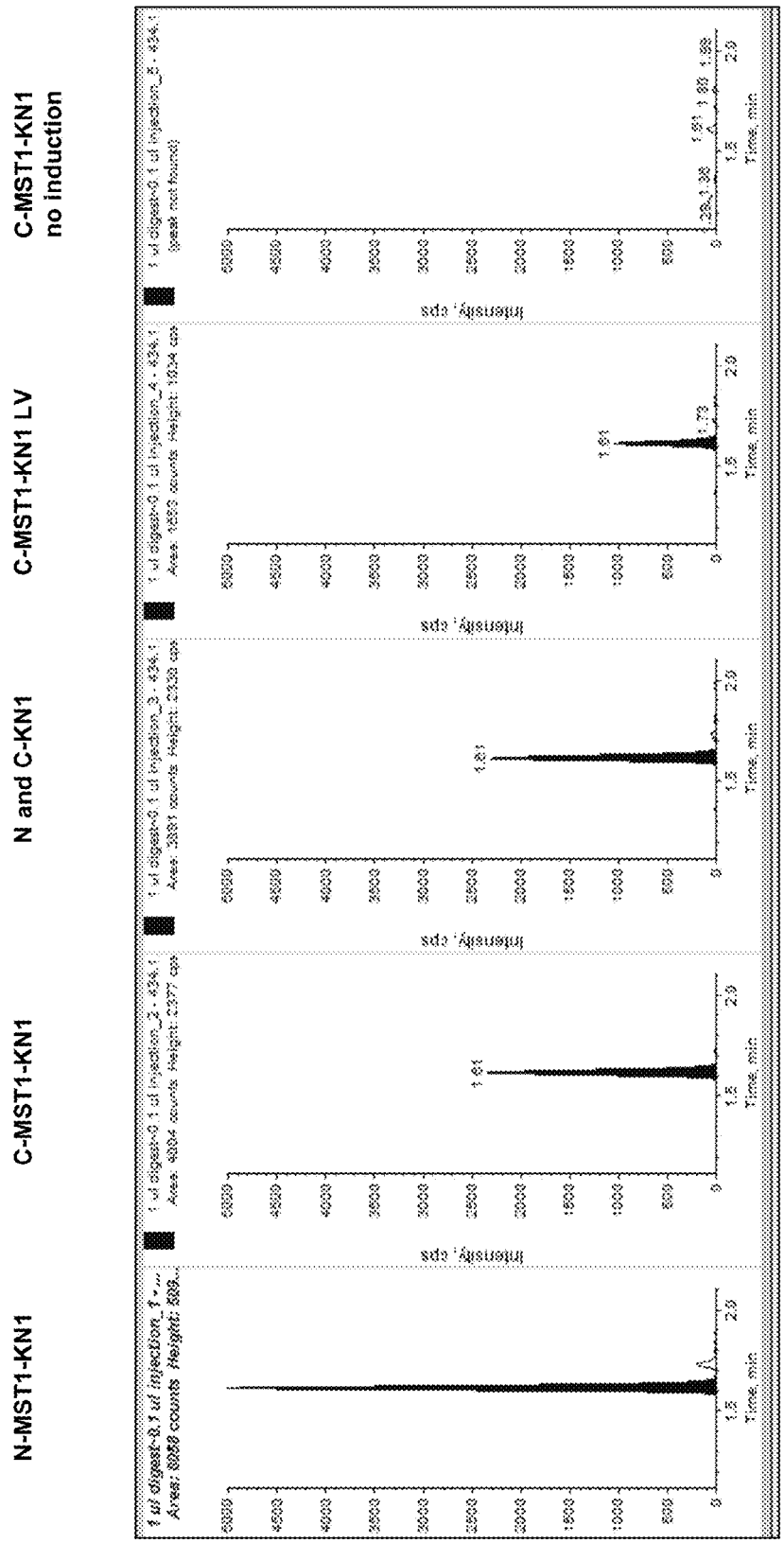
FIG. 4 shows an analysis of MST-KN1 protein extracts by LC-MS/MS.

Following sample preparation, tryptic digestion and acidification with formic acid, MST-KN1 polypeptides were detected by LC-MS/MS. N-MST-KN1, C-MST-KN1, N- and C-KN1 and C-MST-KN1 LV were all detectable as peaks eluting at approximately 1.61 minutes, with peak areas calculated as 8058, 4004, 3891 and 1653 counts for each polypeptide, respectively (FIG. 4). Cells that were transfected to express C-MST1-KN1, but not induced with IPTG, had no detectable peak at the same retention time.

Example 2

Detection of Double-Tagged MST-KN1 Polypeptides in Cell Extracts

Constructs for two double-tagged MST-KN1 polypeptides were created and transfected into *E. coli* for expression. Cells were subsequently treated with IPTG to induce the expression of MST2-KN1-MST3 (SEQ ID NO: 30), or MTS3-KN1-MST2 (SEQ ID NO: 31).

Figure 5:
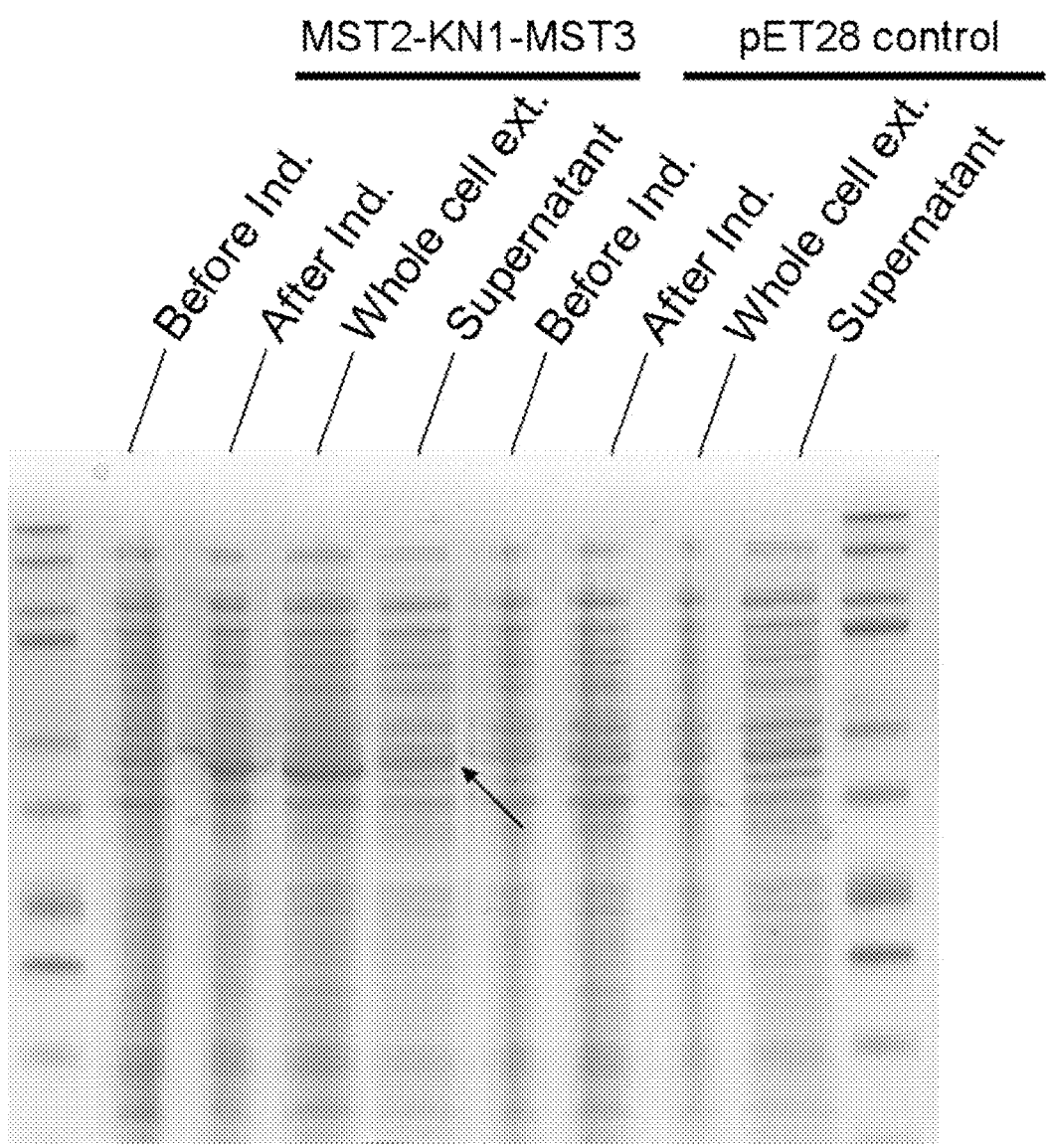
FIG. 5 shows induction of MST2-KN1-MST3 polypeptides and analysis of protein extracts by total protein staining.

Coomassie blue staining clearly demonstrated induction of the MST2-KN1-MST3 polypeptide in both the polypeptide extract and the whole cell extract of cells induced with IPTG when compared to extracts collected prior to induction with IPTG or cells transfected with a vector (pET28) control (FIG. 5).

Figure 6:
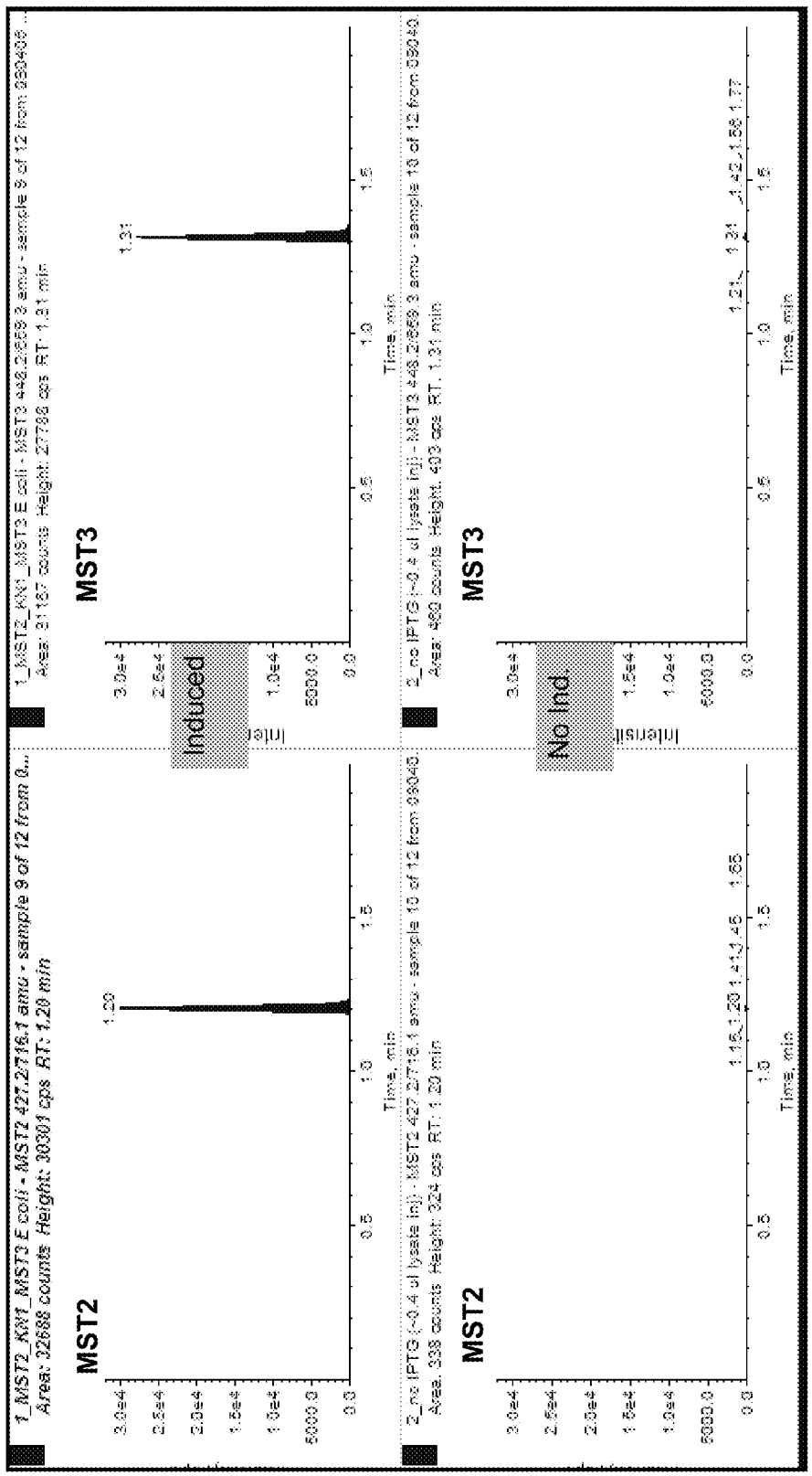
FIG. 6 shows an analysis of MST2-KN1-MST3 protein extracts by LC-MS/MS with and without induction by IPTG.

Following sample preparation, tryptic digestion and acidification with formic acid, the MST2-KN1-MST3 polypeptides were detected by LC-MS/MS. Both the MST2 and MST3 universal peptide tags were separately detected at retention times of 1.2 minutes and 1.31 minutes, respectively, in samples from cells induced with IPTG (FIG. 6). By comparison, extracts from cells that were not induced with IPTG did not generate detectable peaks at similar retention times to the induced samples.

Example 3

Detection of MST-KN1 Polypeptides in Spiked Maize Leaf Extracts

Figure 7:
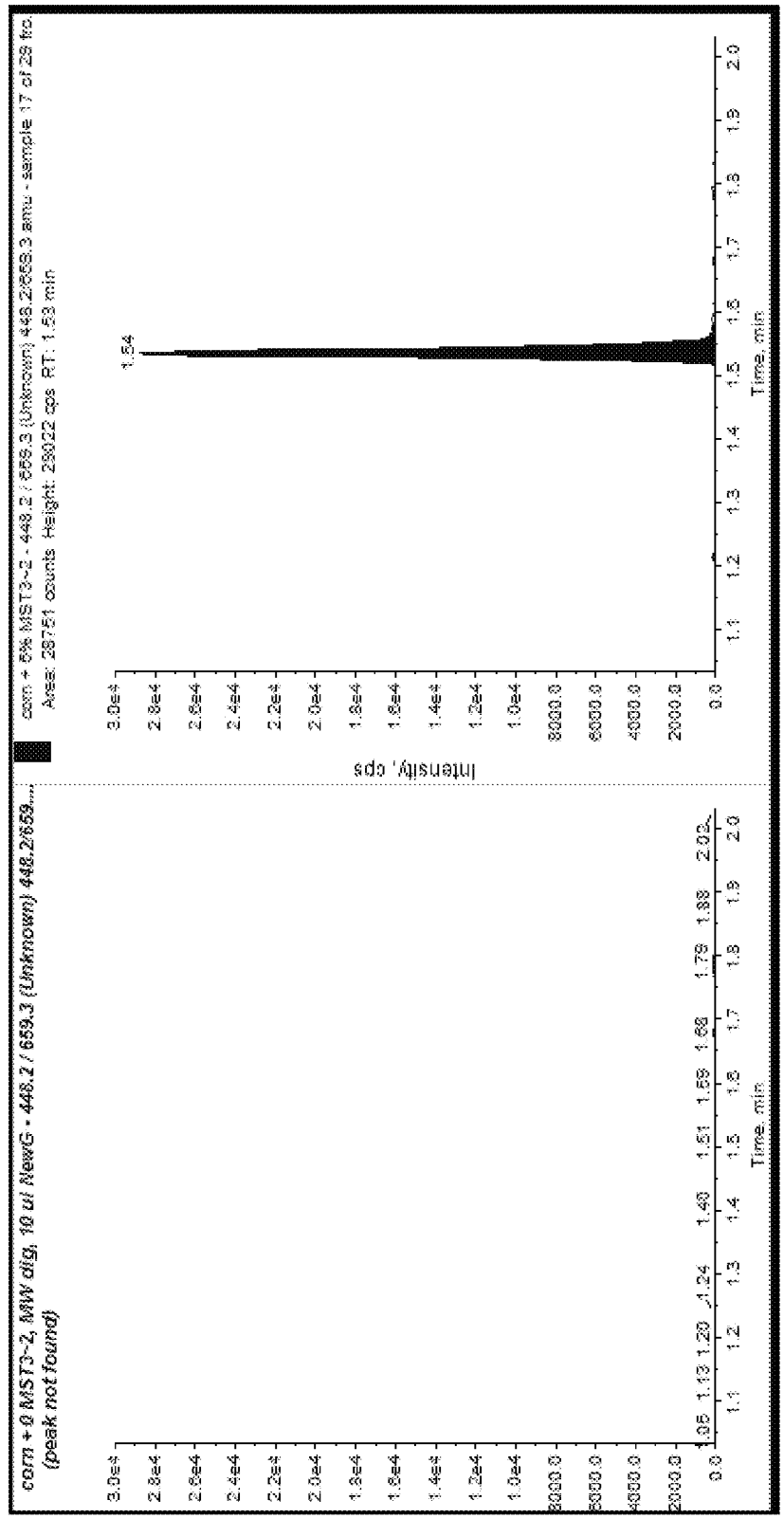
FIG. 7 shows LC-MS/MS analysis of maize leaf extracts spiked with MST3-KN1-MST2.

E. coli extract containing MST3-KN1-MST2 polypeptide from was added to maize leaf extract (5% volume/volume). Following sample preparation including tryptic digestion and acidification with formic acid, the MST3-KN1-MST2 polypeptides were detected in the maize leaf extract by detecting of universal peptide tags with LC-MS/MS (FIG. 7). The retention times of these peptide tags were confirmed by synthetic peptides. No interference peaks were found in the negative control samples where no MST3-KN1-MST2 polypeptide solution was spiked.

Example 4

Agrobacterium-Mediated Transient Expression in Tobacco

The MST3 universal peptide tag was fused to the N-terminus or C-terminus of the C. subvermispora-oxox (Cs-oxox) protein and the DsRed2 fluorescent protein. Agrobacterium tumefaciens strain LBA4044 carrying these fusion proteins were infiltrated into leaves of N. benthamiana (tobacco) essentially as described previously (Tai et al. (1999) PNAS 96:14153-14158; Leister et al. (2005) Plant Cell 17: 1268-78). Leaf punches were collected two days after growing under constant bench light. For detection of the C-terminal universal peptide tags by mass spectrometry, 10 mg of lyophilized leaf tissues were extracted with 600 µL of PBST buffer, and 50 µA of the resulting extract was diluted with 60 µL of 50 mM ABC buffer. Samples were then subjected to microwave digestion for 30 min (45° C. and 50 W) and 6 µA of 10% formic acid was added to each sample. Subsequently, 20 µA of each sample was injected on Q-TRAP 4000 to monitor MST3 with an Aquasil C18 3.5 µm column.

Figure 8:
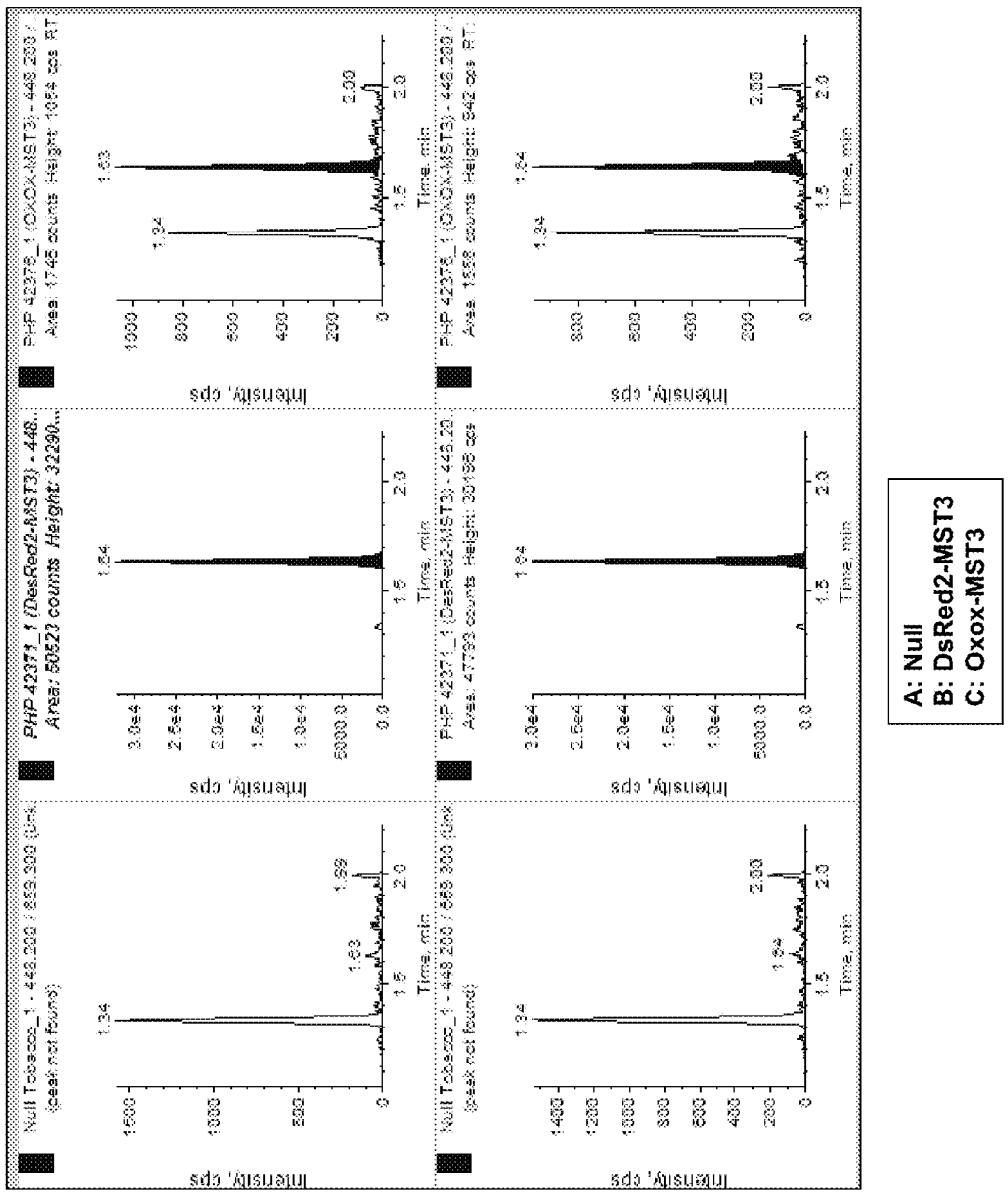
FIG. 8 shows LC-MS/MS analysis of leaf extracts from tobacco plants transiently transfected to express Cs-oxox or DsRed2 proteins that comprise C-terminal MST3 universal peptide tags.

As shown in FIG. 8, no detectable peaks were observed in samples extracted from null tobacco plant leaf extracts which were incorporated into the experiment as controls (panel A, top and bottom). The DsRed2 fluorescent protein, (panel B, top and bottom) exhibited a significant peak at 1.64 minutes in both replicates that represented the C-terminal MST3 universal peptide tag, with the peaks having areas of 50,523 and 47,793, as shown in Table 2 below. The Cs-oxox protein (panel C, top and bottom) also exhibited a significant peak at 1.63 or 1.64 minutes in each replicate that represented the C-terminal MST3 universal peptide tag, with peak areas of 1746 and 1556.

TABLE 2

Peak areas of C-terminal MST3 universal peptide tags detected by mass spectrometry in transiently transfected tobacco leaf extracts.

| Sample No. | Sample | MST3 Peak Area |
|---|---|---|
| 1 | Null tobacco | 0 |
| 2 | PHP__42371__1 (DsRed2-MST3) | 50,523 |
| 3 | PHP__42371__1 (Cs-oxox-MST3) | 1,746 |
| 4 | Null tobacco | 0 |
| 5 | PHP__42371__1 (DsRed2-MST3) | 47,793 |
| 6 | PHP__42371__1 (Cs-oxox-MST3) | 1,556 |

Table 3 shows the peak areas observed upon mass spectrometry analysis of extracted leaf punches from tobacco transiently transfected to express Cs-oxox or DsRed2 with N-terminal MST3 universal peptide tags. Tobacco plants were transfected, extracted and subjected to mass spectrometry analysis as described above for the C-terminal universal peptide tags with the exception that a BEH C18 1.7 µm column was used for separation. As shown in Table 3, no detectable peaks were observed in samples extracted from null tobacco plants which were used as controls. Peaks areas were observed in each of the DsRed2 samples having N-terminal MST3 universal peptide tags, with peak areas of 150, 742, 118,756 and 133,895 respectively, for each of the three replicates tested. No peak areas were detected for Cs-oxox tagged with an N-terminal MST3 universal peptide tag; however, the lack of a peak was the result of the universal peptide tag being positioned upstream of a BAA SS signal peptide in the vector PHP42666. As such, the MST3 was cleaved from the Cs-oxox protein upon removal of the signal peptide by the transfected cells.

TABLE 3

Peak areas of N-terminal MST3 universal peptide tags detected by mass spectrometry in transiently transfected tobacco leaf extracts.

| Sample No. | Sample | MST3 Peak Area |
|---|---|---|
| 1 | Null tobacco | 0 |
| 2 | Null tobacco | 0 |
| 3 | PHP42666 (MST3-Cs-oxox) | 0 |
| 4 | PHP42666 (MST3-Cs-oxox) | 0 |
| 5 | PHP42666 (MST3-Cs-oxox) | 0 |
| 6 | PHP42371 (MST3-DsRed2) | 150,742 |
| 7 | PHP42371 (MST3-DsRed2) | 118,756 |
| 8 | PHP42371 (MST3-DsRed2) | 133,895 |
| 9 | MST2__3 Standard | 22,743 |

The invention claimed is:

1. A method of determining the concentration of a polypeptide in a cell or part thereof, wherein said polypeptide comprises at least one universal peptide tag that is incorporated into the amino acid sequence of said polypeptide, and wherein said polypeptide does not comprise an epitope tag, said method comprising:
   a. analyzing a sample for the presence of said at least one universal peptide tag in said host, or cell or part thereof, wherein said analysis is performed by mass spectrometry, and further wherein said at least one universal peptide tag remains intact;
   b. detecting the presence of said polypeptide based on the presence of said at least one universal peptide tag in said sample;
   c. determining the concentration of said at least one universal peptide tag in said cell, or part thereof; and,
   d. calculating the concentration of said polypeptide based on the concentration of said at least one universal peptide tag in said sample.

2. The method of claim 1, wherein said at least one universal peptide tag comprises the amino acid sequence set forth in SEQ ID NO: 1, or an amino acid sequence having one substitution when compared to the amino acid sequence set forth in SEQ ID NO: 1, wherein said at least one universal peptide tag can be detected by mass spectrometry and can be used to determine the presence or concentration of said polypeptide in a sample.

3. The method of claim 1, wherein said at least one universal peptide tag is fused to the N-terminus of the polypeptide, is fused to the C-terminus of the polypeptide, or is incorporated into the amino acid sequence of the polypeptide and is not located at the N-terminus or C-terminus.

4. The method of claim 1, wherein a linker peptide is positioned between said at least one universal peptide tag and the amino acid sequence of said polypeptide.

5. The method of claim 4, wherein said linker peptide comprises an amino acid sequence set forth in SEQ ID NO: 13.

6. The method of claim 1, wherein said polypeptide is encoded by a polynucleotide comprising a nucleotide sequence, wherein said nucleotide sequence encodes a polypeptide comprising the amino acid sequence set forth in SEQ ID NO: 1, or an amino acid sequence having one substitution when compared to the amino acid sequence set forth in SEQ ID NO: 1.

7. The method of claim 1, wherein said cell is a bacteria, a virus, or a yeast.

8. The method of claim 2, wherein said at least one universal peptide tag comprises the amino acid sequence set forth in SEQ ID NO:1.

9. The method of claim 6, wherein said nucleotide sequence encodes a polypeptide having the amino acid sequence set forth in SEQ ID NO: 1.

10. The method of claim 6, wherein said nucleotide sequence comprises SEQ ID NO: 2.

* * * * *

SEQUENCE LISTING

<160> NUMBER OF SEQ ID NOS: 31

<210> SEQ ID NO 1
<211> LENGTH: 8

```
<212> TYPE: PRT
<213> ORGANISM: Artificial Sequence
<220> FEATURE:
<223> OTHER INFORMATION: MST1

<400> SEQUENCE: 1

Lys His Ala Glu Glu Ile Leu Arg
 1               5

<210> SEQ ID NO 2
<211> LENGTH: 27
<212> TYPE: DNA
<213> ORGANISM: Artificial Sequence
<220> FEATURE:
<223> OTHER INFORMATION: MST1 nucleotide sequence

<400> SEQUENCE: 2
aaacacgctg aagaaattct tcgttag                                          27

<210> SEQ ID NO 3
<211> LENGTH: 8
<212> TYPE: PRT
<213> ORGANISM: Artificial Sequence
<220> FEATURE:
<223> OTHER INFORMATION: MST2

<400> SEQUENCE: 3

Lys His Gly Glu Glu Ile Leu Arg
 1               5

<210> SEQ ID NO 4
<211> LENGTH: 27
<212> TYPE: DNA
<213> ORGANISM: Artificial Sequence
<220> FEATURE:
<223> OTHER INFORMATION: MST2 nucleotide sequence

<400> SEQUENCE: 4
aaacacggtg aagaaattct tcgttag                                          27

<210> SEQ ID NO 5
<211> LENGTH: 8
<212> TYPE: PRT
<213> ORGANISM: Artificial Sequence
<220> FEATURE:
<223> OTHER INFORMATION: MST3

<400> SEQUENCE: 5

Lys His Val Glu Glu Ile Leu Arg
 1               5

<210> SEQ ID NO 6
<211> LENGTH: 27
<212> TYPE: DNA
<213> ORGANISM: Artificial Sequence
<220> FEATURE:
<223> OTHER INFORMATION: MST3 nucleotide sequence

<400> SEQUENCE: 6
aaacacgtgg aagaaattct tcgttag                                          27

<210> SEQ ID NO 7
<211> LENGTH: 10
<212> TYPE: PRT
<213> ORGANISM: Artificial Sequence
<220> FEATURE:
<223> OTHER INFORMATION: MST1-N
```

```
<400> SEQUENCE: 7

Met Ile Lys His Ala Glu Glu Ile Leu Arg
 1               5                   10

<210> SEQ ID NO 8
<211> LENGTH: 30
<212> TYPE: DNA
<213> ORGANISM: Artificial Sequence
<220> FEATURE:
<223> OTHER INFORMATION: MST1-N nucleotide sequence

<400> SEQUENCE: 8
atgattaaac acgctgaaga aattcttcgt                                      30

<210> SEQ ID NO 9
<211> LENGTH: 10
<212> TYPE: PRT
<213> ORGANISM: Artificial Sequence
<220> FEATURE:
<223> OTHER INFORMATION: MST2-N

<400> SEQUENCE: 9

Met Ile Lys His Gly Glu Glu Ile Leu Arg
 1               5                   10

<210> SEQ ID NO 10
<211> LENGTH: 30
<212> TYPE: DNA
<213> ORGANISM: Artificial Sequence
<220> FEATURE:
<223> OTHER INFORMATION: MST2-N nucleotide sequence

<400> SEQUENCE: 10
atgattaaac acggtgaaga aattcttcgt                                      30

<210> SEQ ID NO 11
<211> LENGTH: 10
<212> TYPE: PRT
<213> ORGANISM: Artificial Sequence
<220> FEATURE:
<223> OTHER INFORMATION: MST3-N

<400> SEQUENCE: 11

Met Ile Lys His Val Glu Glu Ile Leu Arg
 1               5                   10

<210> SEQ ID NO 12
<211> LENGTH: 30
<212> TYPE: DNA
<213> ORGANISM: Artificial Sequence
<220> FEATURE:
<223> OTHER INFORMATION: MST3-N nucleotide sequence

<400> SEQUENCE: 12
atgattaaac acgtggaaga aattcttcgt                                      30

<210> SEQ ID NO 13
<211> LENGTH: 2
<212> TYPE: PRT
<213> ORGANISM: Artificial Sequence
<220> FEATURE:
<223> OTHER INFORMATION: Linker Peptide

<400> SEQUENCE: 13

Leu Val
```

1

```
<210> SEQ ID NO 14
<211> LENGTH: 6
<212> TYPE: DNA
<213> ORGANISM: Artificial Sequence
<220> FEATURE:
<223> OTHER INFORMATION: Linker Peptide nucleotide sequence

<400> SEQUENCE: 14 ctagtt                                                              6

<210> SEQ ID NO 15
<211> LENGTH: 146
<212> TYPE: PRT
<213> ORGANISM: Artificial Sequence
<220> FEATURE:
<223> OTHER INFORMATION: GAT4601

<400> SEQUENCE: 15

Met Ile Glu Val Lys Pro Ile Asn Ala Glu Asp Thr Tyr Glu Leu Arg
  1               5                  10                  15

His Arg Ile Leu Arg Pro Asn Gln Pro Ile Glu Ala Cys Met Phe Glu
             20                  25                  30

Ser Asp Leu Leu Arg Gly Ala Phe His Leu Gly Gly Phe Tyr Arg Gly
         35                  40                  45

Lys Leu Ile Ser Ile Ala Ser Phe His Gln Ala Glu His Ser Glu Leu
     50                  55                  60

Gln Gly Gln Lys Gln Tyr Gln Leu Arg Gly Met Ala Thr Leu Glu Gly
 65                  70                  75                  80

Tyr Arg Glu Gln Lys Ala Gly Ser Thr Leu Val Lys His Ala Glu Glu
                 85                  90                  95

Ile Leu Arg Lys Arg Gly Ala Asp Met Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Ile Phe Asp Thr Pro Pro Val Gly Pro His Ile Leu Met Tyr Lys Arg
    130                 135                 140

Ile Thr
145

<210> SEQ ID NO 16
<211> LENGTH: 146
<212> TYPE: PRT
<213> ORGANISM: Artificial Sequence
<220> FEATURE:
<223> OTHER INFORMATION: GAT4604

<400> SEQUENCE: 16

Met Ile Glu Val Lys Pro Ile Asn Ala Glu Asp Thr Tyr Glu Leu Arg
  1               5                  10                  15

His Arg Val Leu Arg Pro Asn Gln Pro Ile Glu Ala Cys Ile Phe Glu
             20                  25                  30

Ser Asp Leu Met Arg Gly Ala Phe His Leu Gly Gly Phe Tyr Gly Gly
         35                  40                  45

Arg Leu Ile Ser Val Ala Ser Phe His Gln Ala Glu His Ser Glu Leu
     50                  55                  60

Gln Gly Gln Lys Gln Tyr Gln Leu Arg Gly Met Ala Thr Leu Glu Gly
 65                  70                  75                  80
```

-continued

```
Tyr Arg Glu Gln Lys Ala Gly Ser Ser Leu Val Lys His Ala Glu Glu
                85                  90                  95

Ile Leu Arg Lys Arg Gly Ala Asp Leu Leu Trp Cys Asn Ala Arg Thr
            100                 105                 110

Ser Ala Ser Gly Tyr Tyr Lys Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 17
<211> LENGTH: 146
<212> TYPE: PRT
<213> ORGANISM: Artificial Sequence
<220> FEATURE:
<223> OTHER INFORMATION: GAT4618

<400> SEQUENCE: 17

Met Ile Glu Val Lys Pro Ile Asn Ala Glu Asp Thr Tyr Asp Leu Arg
1               5                   10                  15

His Arg Val Leu Arg Pro Asn Gln Pro Ile Glu Ala Cys Met Phe Glu
            20                  25                  30

Ser Asp Leu Thr Arg Ser Ala Phe His Leu Gly Gly Phe Tyr Gly Gly
        35                  40                  45

Lys Leu Ile Ser Val Ala Ser Phe His Gln Ala Glu His Ser Glu Leu
    50                  55                  60

Gln Gly Lys Lys Gln Tyr Gln Leu Arg Gly Val Ala Thr Leu Glu Gly
65                  70                  75                  80

Tyr Arg Glu Gln Lys Ala Gly Ser Ser Leu Val Lys His Ala Glu Glu
                85                  90                  95

Ile Leu Arg Lys Arg Gly Ala Asp Met Ile Trp Cys Asn Ala Arg Thr
            100                 105                 110

Ser Ala Ser Gly Tyr Tyr Arg Lys Leu Gly Phe Ser Glu Gln Gly Glu
        115                 120                 125

Val Phe Asp Thr Pro Pro Val Gly Pro His Ile Leu Met Tyr Lys Arg
    130                 135                 140

Ile Thr
145

<210> SEQ ID NO 18
<211> LENGTH: 147
<212> TYPE: PRT
<213> ORGANISM: Artificial Sequence
<220> FEATURE:
<223> OTHER INFORMATION: GAT4621

<400> SEQUENCE: 18

Met Ala Ile Glu Val Lys Pro Ile Asn Ala Glu Asp Thr Tyr Asp Leu
1               5                   10                  15

Arg His Arg Val Leu Arg Pro Asn Gln Pro Ile Glu Ala Cys Met Phe
            20                  25                  30

Glu Ser Asp Leu Thr Arg Ser Ala Phe His Leu Gly Gly Phe Tyr Gly
        35                  40                  45

Gly Lys Leu Ile Ser Val Ala Ser Phe His Ala Glu His Ser Glu
    50                  55                  60

Leu Gln Gly Lys Lys Gln Tyr Gln Leu Arg Gly Val Ala Thr Leu Glu
65                  70                  75                  80
```

```
Gly Tyr Arg Glu Gln Lys Ala Gly Ser Ser Leu Val Lys His Ala Glu
                85                  90                  95

Glu Ile Leu Arg Lys Arg Gly Ala Asp Met Ile Trp Cys Asn Ala Arg
            100                 105                 110

Thr Ser Ala Ser Gly Tyr Tyr Arg Lys Leu Gly Phe Ser Glu Gln Gly
        115                 120                 125

Glu Val Phe Asp Thr Pro Pro Val Gly Pro His Ile Leu Met Tyr Lys
    130                 135                 140

Arg Ile Thr
145

<210> SEQ ID NO 19
<211> LENGTH: 25
<212> TYPE: PRT
<213> ORGANISM: Zymomonas mobilis

<400> SEQUENCE: 19

Gly Ser Ala Leu Leu Lys His Ala Met Glu Lys Leu Val Thr Pro Asp
1               5                   10                  15

Leu Thr Glu Ile Trp Leu Asn Ala Arg
            20                  25

<210> SEQ ID NO 20
<211> LENGTH: 25
<212> TYPE: PRT
<213> ORGANISM: Bacillus cereus

<400> SEQUENCE: 20

Gly Ser Ser Leu Ile Gln Lys Ala Glu Gln Ile Leu Gln Glu Arg Gln
1               5                   10                  15

Ala Asn Met Leu Trp Cys Asn Gly Arg
            20                  25

<210> SEQ ID NO 21
<211> LENGTH: 25
<212> TYPE: PRT
<213> ORGANISM: Listeria innocua

<400> SEQUENCE: 21

Gly Arg Ala Leu Leu Ala Glu Gly Glu Ala Glu Ile Trp Lys His Gly
1               5                   10                  15

Ala Asp Ile Ile Trp Cys Asn Ala Arg
            20                  25

<210> SEQ ID NO 22
<211> LENGTH: 25
<212> TYPE: PRT
<213> ORGANISM: Chloroflexus aurantiacus

<400> SEQUENCE: 22

Gly Thr Ala Leu Leu Asp Ala Gly Ile His Tyr Val Lys Gln Gln Arg
1               5                   10                  15

Gly Asp Leu Val Trp Cys His Gly Arg
            20                  25

<210> SEQ ID NO 23
<211> LENGTH: 25
<212> TYPE: PRT
<213> ORGANISM: Vibrio parahaemolyticus

<400> SEQUENCE: 23
```

```
Gly Ser Arg Met Leu Glu Met Met Ile Glu Asp Ala Arg Ala Leu Asn
1               5                   10                  15

Ser Glu Val Phe Trp Cys Asp Ala Arg
            20                  25

<210> SEQ ID NO 24
<211> LENGTH: 19
<212> TYPE: PRT
<213> ORGANISM: Artificial Sequence
<220> FEATURE:
<223> OTHER INFORMATION: Consensus sequence

<400> SEQUENCE: 24

Gly Ser Ala Leu Leu Ala Glu Glu Leu Arg Ala Asp Leu Ile Trp Cys
1               5                   10                  15

Asn Ala Arg

<210> SEQ ID NO 25
<211> LENGTH: 33
<212> TYPE: DNA
<213> ORGANISM: Artificial Sequence
<220> FEATURE:
<223> OTHER INFORMATION: LN-MST1-N nucleotide sequence

<400> SEQUENCE: 25
ctagttaaac acgctgaaga aattcttcgt tag                               33

<210> SEQ ID NO 26
<211> LENGTH: 10
<212> TYPE: PRT
<213> ORGANISM: Artificial Sequence
<220> FEATURE:
<223> OTHER INFORMATION: LN-MST1-N

<400> SEQUENCE: 26

Leu Val Lys His Ala Glu Glu Ile Leu Arg
1               5                   10

<210> SEQ ID NO 27
<211> LENGTH: 7
<212> TYPE: PRT
<213> ORGANISM: Artificial Sequence
<220> FEATURE:
<223> OTHER INFORMATION: GAT4621 Peptide

<400> SEQUENCE: 27

His Ala Glu Glu Ile Leu Arg
1               5

<210> SEQ ID NO 28
<211> LENGTH: 7
<212> TYPE: PRT
<213> ORGANISM: Artificial Sequence
<220> FEATURE:
<223> OTHER INFORMATION: GAT4621 Peptide

<400> SEQUENCE: 28

His Gly Glu Glu Ile Leu Arg
1               5

<210> SEQ ID NO 29
<211> LENGTH: 7
<212> TYPE: PRT
<213> ORGANISM: Artificial Sequence
<220> FEATURE:
```

<223> OTHER INFORMATION: GAT4621 Peptide

<400> SEQUENCE: 29

His Val Glu Glu Ile Leu Arg
1               5

<210> SEQ ID NO 30
<211> LENGTH: 377
<212> TYPE: PRT
<213> ORGANISM: Artificial Sequence
<220> FEATURE:
<223> OTHER INFORMATION: MST2-KN1-MST3

<400> SEQUENCE: 30

Met Ile Lys His Gly Glu Glu Ile Leu Arg Met Glu Ile Thr Gln
1               5                   10                  15

His Phe Gly Val Gly Ala Ser Ser His Gly His Gly His Gly Gln His
            20                  25                  30

His His His His His His His Pro Trp Ala Ser Ser Leu Ser Ala
        35                  40                  45

Val Val Ala Pro Leu Pro Pro Gln Pro Pro Ser Ala Gly Leu Pro Leu
50                  55                  60

Thr Leu Asn Thr Val Ala Ala Thr Gly Asn Ser Gly Gly Ser Gly Asn
65                  70                  75                  80

Pro Val Leu Gln Leu Ala Asn Gly Gly Gly Leu Leu Asp Ala Cys Val
                85                  90                  95

Lys Ala Lys Glu Pro Ser Ser Ser Pro Tyr Ala Gly Asp Val Glu
            100                 105                 110

Ala Ile Lys Ala Lys Ile Ile Ser His Pro His Tyr Tyr Ser Leu Leu
            115                 120                 125

Thr Ala Tyr Leu Glu Cys Asn Lys Val Gly Ala Pro Pro Glu Val Ser
    130                 135                 140

Ala Arg Leu Thr Glu Ile Ala Gln Glu Val Glu Ala Arg Gln Arg Thr
145                 150                 155                 160

Ala Leu Gly Gly Leu Ala Ala Ala Thr Glu Pro Glu Leu Asp Gln Phe
                165                 170                 175

Met Glu Ala Tyr His Glu Met Leu Val Lys Phe Arg Glu Glu Leu Thr
            180                 185                 190

Arg Pro Leu Gln Glu Ala Met Glu Phe Met Arg Arg Val Glu Ser Gln
        195                 200                 205

Leu Asn Ser Leu Ser Ile Ser Gly Arg Ser Leu Arg Asn Ile Leu Ser
    210                 215                 220

Ser Gly Ser Ser Glu Glu Asp Gln Glu Gly Ser Gly Gly Glu Thr Glu
225                 230                 235                 240

Leu Pro Glu Val Asp Ala His Gly Val Asp Gln Glu Leu Lys His His
                245                 250                 255

Leu Leu Lys Lys Tyr Ser Gly Tyr Leu Ser Ser Leu Lys Gln Glu Leu
            260                 265                 270

Ser Lys Lys Lys Lys Lys Gly Lys Leu Pro Lys Glu Ala Arg Gln Gln
        275                 280                 285

Leu Leu Ser Trp Trp Asp Gln His Tyr Lys Trp Pro Tyr Pro Ser Glu
    290                 295                 300

Thr Gln Lys Val Ala Leu Ala Glu Ser Thr Gly Leu Asp Leu Lys Gln
305                 310                 315                 320

Ile Asn Asn Trp Phe Ile Asn Gln Arg Lys Arg His Trp Lys Pro Ser
                325                 330                 335

```
Glu Met His His Leu Met Met Asp Gly Tyr His Thr Thr Asn Ala
        340                 345                 350

Phe Tyr Met Asp Gly His Phe Ile Asn Asp Gly Leu Tyr Arg Leu
        355                 360                 365

Gly Lys His Val Glu Glu Ile Leu Arg
        370                 375

<210> SEQ ID NO 31
<211> LENGTH: 377
<212> TYPE: PRT
<213> ORGANISM: Artificial Sequence
<220> FEATURE:
<223> OTHER INFORMATION: MST3-KN1-MST2

<400> SEQUENCE: 31

Met Ile Lys His Val Glu Ile Leu Arg Met Glu Glu Ile Thr Gln
  1               5                  10                  15

His Phe Gly Val Gly Ala Ser Ser His Gly His Gly His Gln His
                 20                  25                  30

His His His His His His His Pro Trp Ala Ser Ser Leu Ser Ala
             35                  40                  45

Val Val Ala Pro Leu Pro Gln Pro Pro Ser Ala Gly Leu Pro Leu
 50                  55                  60

Thr Leu Asn Thr Val Ala Ala Thr Gly Asn Ser Gly Gly Ser Gly Asn
 65                  70                  75                  80

Pro Val Leu Gln Leu Ala Asn Gly Gly Gly Leu Leu Asp Ala Cys Val
                 85                  90                  95

Lys Ala Lys Glu Pro Ser Ser Ser Pro Tyr Ala Gly Asp Val Glu
                100                 105                 110

Ala Ile Lys Ala Lys Ile Ile Ser His Pro His Tyr Tyr Ser Leu Leu
                115                 120                 125

Thr Ala Tyr Leu Glu Cys Asn Lys Val Gly Ala Pro Pro Glu Val Ser
130                 135                 140

Ala Arg Leu Thr Glu Ile Ala Gln Glu Val Glu Ala Arg Gln Arg Thr
145                 150                 155                 160

Ala Leu Gly Gly Leu Ala Ala Ala Thr Glu Pro Glu Leu Asp Gln Phe
                165                 170                 175

Met Glu Ala Tyr His Glu Met Leu Val Lys Phe Arg Glu Glu Leu Thr
                180                 185                 190

Arg Pro Leu Gln Glu Ala Met Glu Phe Met Arg Arg Val Glu Ser Gln
                195                 200                 205

Leu Asn Ser Leu Ser Ile Ser Gly Arg Ser Leu Arg Asn Ile Leu Ser
                210                 215                 220

Ser Gly Ser Ser Glu Glu Asp Gln Glu Gly Gly Gly Glu Thr Glu
225                 230                 235                 240

Leu Pro Glu Val Asp Ala His Gly Val Asp Gln Glu Leu Lys His His
                245                 250                 255

Leu Leu Lys Lys Tyr Ser Gly Tyr Leu Ser Ser Leu Lys Gln Glu Leu
                260                 265                 270

Ser Lys Lys Lys Lys Gly Lys Leu Pro Lys Glu Ala Arg Gln Gln
                275                 280                 285

Leu Leu Ser Trp Trp Asp Gln His Tyr Lys Trp Pro Tyr Pro Ser Glu
                290                 295                 300

Thr Gln Lys Val Ala Leu Ala Glu Ser Thr Gly Leu Asp Leu Lys Gln
305                 310                 315                 320
```

```
Ile Asn Asn Trp Phe Ile Asn Gln Arg Lys Arg His Trp Lys Pro Ser
                325             330             335

Glu Glu Met His His Leu Met Met Asp Gly Tyr His Thr Thr Asn Ala
            340             345             350

Phe Tyr Met Asp Gly His Phe Ile Asn Asp Gly Gly Leu Tyr Arg Leu
        355             360             365

Gly Lys His Gly Glu Glu Ile Leu Arg
    370             375
```